(12) United States Patent
Napier et al.

(10) Patent No.: US 7,605,170 B2
(45) Date of Patent: Oct. 20, 2009

(54) 8-AZABICYCLO[3.2.1]OCTANE DERIVATIVES

(75) Inventors: Susan Elizabeth Napier, Newhouse (GB); Matilda Jane Bingham, Newhouse (GB); Neil Andrew Dunbar, Newhouse (GB)

(73) Assignee: N.V. Organon, Oss (NL)

( * ) Notice: Subject to any disclaimer, the term of this patent is extended or adjusted under 35 U.S.C. 154(b) by 0 days.

(21) Appl. No.: 11/607,574

(22) Filed: Dec. 1, 2006

(65) Prior Publication Data
US 2007/0185156 A1 Aug. 9, 2007

Related U.S. Application Data

(60) Provisional application No. 60/741,320, filed on Dec. 1, 2005.

(51) Int. Cl.
C07D 451/00 (2006.01)
A01N 43/42 (2006.01)
A61K 31/44 (2006.01)
(52) U.S. Cl. .................................... 514/304; 546/127
(58) Field of Classification Search ................. 546/127; 514/304
See application file for complete search history.

(56) References Cited

U.S. PATENT DOCUMENTS

| | | | | |
|---|---|---|---|---|
| 3,530,137 A | * | 9/1970 | Doda et al. | 546/127 |
| 5,958,945 A | | 9/1999 | Imbert et al. | |
| 7,199,147 B2 | | 4/2007 | Imazaki et al. | |

FOREIGN PATENT DOCUMENTS

| | | |
|---|---|---|
| EP | 1 403 255 A1 | 3/2004 |
| GB | 1164555 | 9/1969 |
| JP | 04 208267 A | 7/1992 |
| JP | 3087763 | 7/2000 |
| WO | WO 2002/100833 A1 | 12/2002 |
| WO | WO 2003/062235 A1 | 7/2003 |
| WO | WO 2004/043904 A1 | 5/2004 |
| WO | WO 2004/113334 A1 | 12/2004 |
| WO | WO 2005/123728 A1 | 12/2005 |

OTHER PUBLICATIONS

Mochizuki et al., Psychopharmacology, 2002, vol. 162, pp. 323-332.*
Ananthan et al., "Identification of a Novel Partial Inhibitor of Dopamine Transporter Among 4-Substituted 2-Phenylquinazolines," Bioorganic & Medicinal Chemistry Letters, vol. 12, pp. 2225-2228 (2002).
Ley et al., "Modern Synthetic Methods for Copper-Mediated C(aryl)-O, C(aryl)-N, and C(aryl)-S Bond Formation," Angew. Chem. Int. Ed., vol. 42, pp. 5400-5449 (2003).
Written Opinion dated Jun. 3, 2008 for International Application No. PCT/EP2006/069047.

International Search Report mailed Mar. 15, 2007 for International Application No. PCT/EP2006/069047.
Arvanitis et al., "Imidazo[4,5-b]pyridines as Corticotropin Releasing Factor Receptor Ligands," Bioorg. Med. Chem. Lett. 13 (2003) 125-128.
Batt et al., "Regioselectivity in the Acid-Catalyzed Isomerization of 2-Substituted I,4-Dihydro-I,4- epoxynaphthaleness," J. Org. Chem. 56(23) (1991) 6704-6708.
Bell et al., "Regioselective Monomethylation of Unsymmetrical Naphthalenediols with Methanolic HCl," Aust. J. Chem. 46(5) (1993) 731-737.
Boxhall et al., "The Desymmetrisation of Resorcinol: The Synthesis of Resorcinol Monoalkyl Ethers ", Synlett 7 (2003) 997-1001.
Castro et al., "Mitsunobu-like Processes with a Novel Triphenylphosphine-Cyclic Sulfamide Betaine," J. Org. Chem. 59 (1994) 2289-2291.
de Lang et al., "Transition Metal Catalysed Cross-Coupling Between Benzylic Halides and Aryl Nucleophiles. Synthesis of some Toxicologically Interesting Tetrachlorobenzyltoluenes," Tetrahedron 54(12) (1998) 2953-2966.
Den Hertog et al., "The Chloropyridines" Recl. Trav. Chim. Pays-Bas 69 (1950) 673-699.
Derwent Publications, Ltd., London, GB; Class B02, AN 1992-303575; XP002361888 Abstract.
Hulme et al. "Asymmetric Synthesis of the Key Intermediates Leading to (-)-Aphanorphine and (-)-Eptazocine," J. Org. Chem. 60(5) (1995) 1265-1270.
Ito et al., "A New Preparation of Benzofurans Utilizing Trimethylsilyldiazomethane," Synlett 10 (1997) 1163-1164.
Kolder et al., "Synthesis and Reactivity of 5-Chloro-2,4-Dihydroxypyridine," Recl. Trav. Chim. Pays-Bas 72 (1953) 285-295.

(Continued)

Primary Examiner—D. Margaret Seaman
Assistant Examiner—Niloofar Rahmani
(74) Attorney, Agent, or Firm—Susan Hess

(57) ABSTRACT

The present invention relates to a 8-azabicyclo[3.2.1] octane derivative of Formula I,

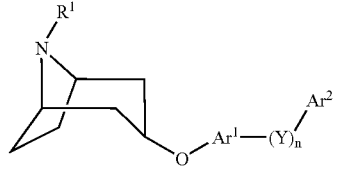

Formula I wherein each of the substituents is given the definition as set forth in the specification and claims, or a pharmaceutically acceptable salt thereof or solvate thereof. The present invention also relates to a pharmaceutical composition comprising an 8-azabicyclo [-3.2.1] octane derivative in admixture with one or more pharmaceutically acceptable auxiliaries and to the use of the 8-azabicyclo[3.2.1] octane derivative in therapy.

14 Claims, No Drawings

OTHER PUBLICATIONS

Kraiss et al., "Chemistry of Tropan-3-yl Ethers. Part I. Synthesis of Tropan-3-yl Ethers," *J. Chem. Soc., Phys. Org.* 11 (1971) 2145-2149.

Momose et al., "Bicyclo[3.3.1]nonanes as synthetic intermediates. Part 19. Asymmetric cleavage of ω-azabicyclo[3.$n$.1]alkan-3-ones at the 'fork head'," *J. Chem. Soc., Perkins Trans. 1*, (1997) 1307-1313.

Mukherjee et al., "Studies in Sulfur Heterocycles. Part 8. 3,4-Dihydro-thieno[2,3-*i*][1]benzoxepin-5(2*H*)-one, a New Heterocyclic System and a Key Intermediate in the Synthesis of Novel Polycondensed Sulfur Heterocycles," *J. Chem. Res.* (S) (1993) 192-193.

Oberhauser, "A New Bronnination Method for Phenols and Anisoles: NBS/HBF$_4$,Et$_2$O in CH$_3$CN," *J. Org. Chem.* 62 (1997) 4504-4506.

Rahman et al., "7-Substituted Benzo[*b*]thiophenes and 1,2-Benzisothiazoles. Part I .Hydroxy- or Methoxy-derivatives," *J. Chem. Soc. (Perkin Trans. 1)* (1983) 2973-2977.

Patent Abstracts of Japan, vol. 016, No. 544 (C-1004), Nov. 13, 1992.

Zambias et al., "The Synthesis of 5-Hydroxy-2,3-Dihydrobenzo(B)Thiophene (1) Via an Efficient One Step Preparation of 5-Nitro-Benzo(B)Thiophene-2-Carboxylate (3A)," *Synth. Comm.* 21(7) (1991) 959-964.

International Search Report mailed Jul. 11, 2006 for International Application No. PCT/EP2006/066896.

Written Opinion mailed Jul. 11, 2006 for International Application No. PCT/EP2006/066896.

* cited by examiner

8-AZABICYCLO[3.2.1]OCTANE DERIVATIVES

The present invention relates to 8-azabicyclo[3.2.1]octane derivatives, to pharmaceutical compositions comprising these compounds and to their use in therapy.

Monoamine reuptake inhibitors have found widespread use in therapy, in particular, in the treatment of depression, a common, serious and life-threatening disorder with persistent and debilitating side-effects. The older tricyclic monoamine reuptake inhibitors, including imipramine and amitriptyline are effective antidepressants but these compounds additionally have deleterious cardiovascular and anticholinergic side-effects which can lead to serious toxicity in overdose and to poor patient compliance. The newer drugs, such as the selective serotonin reuptake inhibitors (SSRIs), whilst being an improvement over older antidepressants have their own particular pattern of side-effects which include sleep disturbances, gastrointestinal symptoms and sexual problems. Monoamine reuptake inhibitors are also indicated to be useful in the treatment of other disorders such as pain, panic disorders, depression, anxiety, attention deficit hyperactivity disorder (ADHD) or obsessive compulsive disorder.

In view of the shortcomings of the currently available monoamine reuptake inhibitors, the search for new compounds which are safe and effective continues. In particular, there has been recently renewed interest in drugs which inhibit monoamine reuptake at one or more of the serotonin, noradrenaline and dopamine transporters.

WO 04/113334 discloses 8-azabicyclo[3.2.1]octane derivatives indicated to be monoamine neurotransmitter reuptake inhibitors and as such useful in the treatment of diseases or disorders responsive to inhibition of monoamine neurotransmitter reuptake in the central nervous system.

A further example of a 8-azabicyclo[3.2.1]octane derivative, shown to bind weakly to serotonin and dopamine transporters is disclosed in *Bioorg. and Med. Chem. Lett.*, 2002, 12, 2225-2228. The 2-phenylquinazoline group is a key feature of all the dopamine transporter ligands disclosed. The 8-azabicyclo[3.2.1]octane derivative disclosed is not indicated to inhibit reuptake of either serotonin or dopamine.

GB 1164555 discloses tropine derivatives, including 8-alkyl-3-aryloxy-8-azabicyclo[3.2.1]octanes indicated to possess effective and unexpected pharmacological properties. 8-Methyl-3-(2-phenylphenoxy)-8-azabicyclo[3.2.1]octane is specifically disclosed.

In a first aspect the present invention provides a 8-azabicyclo[3.2.1]octane derivative of formula I

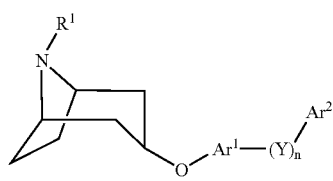

formula I wherein
$R^1$ is H or $C_{1-5}$alkyl;
Y is O, S or $O(CH_2)_m$;
m is 1 or 2;
n is 0 or 1;
$Ar^1$ is phenylene or pyridylene, said phenylene and pyridylene being 1,3-linked with respect to O and when n is 1 with Y and when n is 0 with $Ar^2$, said phenylene or pyridylene being optionally substituted with one or two substituents independently selected from halogen, $C_{1-5}$alkyl, $C_{1-5}$alkoxy, $C_{3-6}$cycloalkyl, $C_{2-5}$alkenyl, $C_{2-5}$alkynyl, phenyl, CN and hydroxy, wherein said $C_{1-5}$alkyl and $C_{1-5}$alkoxy are optionally substituted with one to three halogens and wherein the oxygen of said hydroxy is optionally bonded to $Ar^2$ to form a 5-membered ring;
$Ar^2$ is phenyl or a 5-6 membered heteroaryl, said phenyl or 5-6 membered heteroaryl being optionally substituted with one to three substituents independently selected from halogen, $C_{1-5}$alkyl, $C_{1-5}$alkoxy, CN, $CONR^2R^3$, $CO_2R^4$, $NHCOR^5$ and hydroxy, wherein said $C_{1-5}$alkyl and $C_{1-5}$alkoxy are optionally substituted with one to three halogens and wherein the oxygen of said hydroxy is optionally bonded to $Ar^1$ to form a 5-membered ring;
$R^2$-$R^4$ are independently H or $C_{1-5}$alkyl and
$R^5$ is $C_{1-5}$alkyl
or a pharmaceutically acceptable salt or solvate thereof.

The term $C_{1-5}$alkyl, as used herein, represents a branched or unbranched alkyl group having 1-5 carbon atoms. Examples of such groups are methyl, ethyl, isopropyl, tertiary butyl and pentyl.

The term $C_{1-5}$alkoxy, as used herein, represents a branched or unbranched alkoxy group having 1-5 carbon atoms. Examples of such groups are methoxy, ethoxy, isopropyloxy and tertiary butyloxy.

The term $C_{3-6}$cycloalkyl, as used herein, represents a branched or unbranched cyclic alkyl group having 3-6 carbon atoms. Examples of such groups are cyclopropyl, cyclopentyl and 2-methylcyclopentyl.

The term $C_{2-5}$alkenyl, as used herein, represents a branched or unbranched alkenyl group having 2-5 carbon atoms and at least one double bond. Examples of such groups are ethenyl and propenyl.

The term $C_{2-5}$ alkynyl, as used herein, represents a branched or unbranched alkynyl group having 2-5 carbon atoms and at least one triple bond. Examples of such groups are ethynyl and propynyl.

The term 5-6 membered heteroaryl ring, as used herein, represents a 5-6 membered heteroaromatic ring comprising 1-2 heteroatoms selected from N, O and S. Examples of such groups include furanyl, pyrrolyl, thienyl, pyridinyl, oxazolyl, imidazolyl, thiazolyl and pyrimidinyl.

The term halogen, as used herein, represents a F, Cl, Br or I atom

The skilled person will appreciate that when $Ar^1$ is pyridylene 1,3-linked with respect to O and when n is 1 with Y and when n is 0 with $Ar^2$, the term '1,3-linked' refers to the linking relationship of the pyridylene with respect to O and when n is 1 with Y and when n is 0 with $Ar^2$ and not with respect to the numbering of the pyridylene. Thus the skilled person will appreciate that with respect to the numbering of the pyridylene $Ar^1$ is, for example, a 2,6-pyridylene or a 2,4-pyridylene but not a 1,3-pyridylene.

In one embodiment of the present invention $R^1$ is H.
In a further embodiment $R^1$ is methyl.
In a further embodiment n is 0.
In another embodiment Y is O and n is 1.
In another embodiment $Ar^1$ is phenylene or pyridylene optionally substituted with one or two substituents independently selected from halogen, $C_{1-5}$alkyl, $C_{1-5}$alkoxy, or CN.
In a further embodiment $Ar^1$ is phenylene or pyridylene optionally substituted with one or two substituents independently selected from chloro, fluoro, methyl, methoxy or CN.

A further embodiment of the present invention is a 8-azabicyclo[3.2.1]octane derivative of formula II

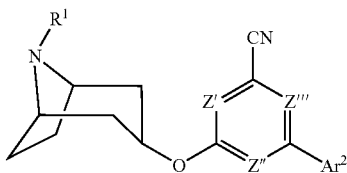

formula II wherein Z', Z" and Z'" are CH or N with the proviso that only one of Z', Z" and Z'" can be N at the same time and wherein R$^1$ and Ar$^2$ have the previously defined meanings. A still further embodiment of the present invention is a 8-azabicyclo[3.2.1]octane derivative of formula II, wherein Z' and Z'" are CH, Z" is CH or N and wherein R$^1$ and Ar$^2$ have the previously defined meanings.

In a further embodiment Ar$^2$ is phenyl or a 5-6 membered heteroaryl, said phenyl or 5-6 membered heteroaryl being optionally substituted with one or two substituents independently selected from halogen, C$_{1-5}$alkyl, C$_{1-5}$alkoxy and CN wherein said C$_{1-5}$alkyl is optionally substituted with 1-3 halogens. In a still further embodiment Ar$^2$ is phenyl or pyridyl said phenyl or pyridyl being optionally substituted with one to two substituents independently selected from chloro, fluoro, methyl, methoxy, CN or CF$_3$.

A further embodiment of the present invention is a 8-azabicyclo[3.2.1]octane derivative of formula III

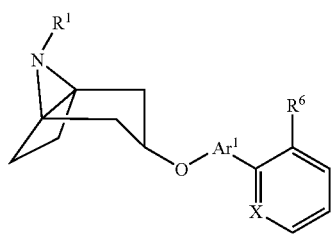

formula III wherein R$^1$ and Ar$^1$ have the previously defined meanings and wherein X is CH or N and R$^6$ is H, methoxy, fluoro, chloro, CN or CF$_3$.

A still further embodiment of the present invention is a 8-azabicyclo[3.2.1]octane derivative of formula IV

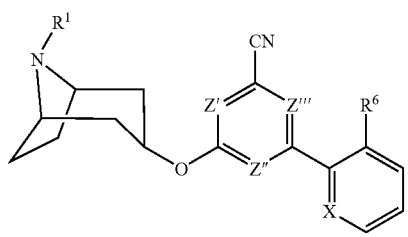

formula IV wherein R$^1$ has the previously defined meanings, Z', Z" and Z'" are CH or N with the proviso that only one of Z', Z" and Z'" can be N at the same time and wherein X is CH or N and R$^6$ is H, methoxy, fluoro, chloro, CN or CF$_3$.

A further embodiment of the present invention is a 8-azabicyclo[3.2.1]octane derivative selected from:

3-exo-(5-chlorobiphenyl-3-yloxy)-8-azabicyclo[3.2.1]octane;

exo 5-(8-azabicyclo[3.2.1]oct-3-yloxy)biphenyl-3-carbonitrile;

exo 3-(8-azabicyclo[3.2.1]oct-3-yloxy)-5-phenoxybenzonitrile;

3-exo-(4'-methoxybiphenyl-3-yloxy)-8-azabicyclo[3.2.1]octane;

exo 3'-(8-azabicyclo[3.2.1]oct-3-yloxy)biphenyl-4-carbonitrile;

3-exo-(3-pyridin-4-ylphenoxy)-8-azabicyclo[3.2.1]octane;

exo 2-{6-(8-azabicyclo[3.2.1]oct-3-yloxy)-4-chloropyridin-2-yl}benzonitrile;

exo 2-(8-azabicyclo[3.2.1]oct-3-yloxy)-6-(2-cyanophenyl)isonicotinonitrile;

exo 3-[(8-azabicyclo[3.2.1]oct-3-yl)oxy]-5-(3-chloropyridin-2-yl)benzonitrile;

exo 3-(8-azabicyclo[3.2.1]oct-3-yloxy)-5-cyanophenyl)nicotinonitrile;

exo 3-(8-azabicyclo[3.2.1]oct-3-yloxy)-5-(3-fluoropyridin-2-yl)benzonitrile;

exo 3'-(8-azabicyclo[3.2.1]oct-3-yloxy)biphenyl-2-carbonitrile;

exo 2-[6-(8-azabicyclo[3.2.1]oct-3-yloxy)pyridin-2-yl]benzonitrile;

3'-(8-azabicyclo[3.2.1]oct-3-exo-yloxy)-2'-fluorobiphenyl-4-carbonitrile and 2-(8-azabicyclo[3.2.1]oct-3-exo-yloxy)-6-phenylisonicotinonitrile or a pharmaceutically acceptable salt or solvate thereof.

The 8-azabicyclo[3.2.1]octane derivatives of formula I are prepared by methods well known in the art of organic chemistry, see for example, J. March, 'Advanced Organic Chemistry' 4$^{th}$ Edition, John Wiley and Sons. During synthetic sequences it may be necessary and/or desirable to protect sensitive or reactive groups on any of the molecules concerned. This is achieved by means of conventional protecting groups, such as those described in T. W. Greene and P. G. M. Wutts 'Protective Groups in Organic Synthesis' 3$^{rd}$ Edition, John Wiley and Sons, 1999. The protective groups are optionally removed at a convenient subsequent stage using methods well known in the art.

Scheme 1

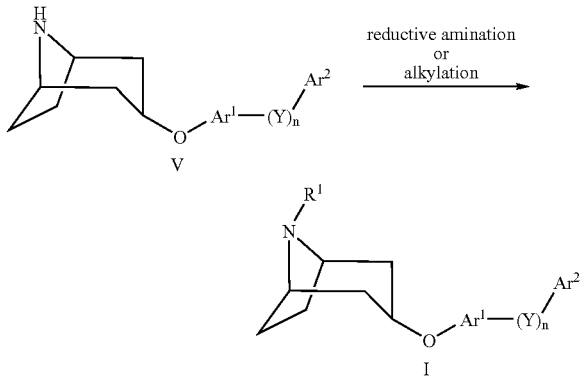

Compounds of formula I, wherein R$^1$, n, Y, Ar$^1$ and Ar$^2$ have the meanings as previously defined (except that R$^1$ is not H), are prepared from compounds of formula V by reductive amination with suitable aldehydes in the presence of a suitable reducing agent such as sodium cyanoborohydride or sodium triacetoxyborohydride in a suitable solvent such as methanol. Alternatively, for example, compounds of formula I can be prepared by alkylation of compounds of formula V with an alkyl halide or an alkyl sulphonate in the presence of a base such as potassium carbonate or cesium carbonate in a suitable solvent such as acetonitrile or ethyl acetate (Scheme 1).

Compounds of general formula V are prepared by substitution of the hydroxyl group in 8-azabicyclo[3.2.1]octan-3-α-ol or 8-azabicyclo[3.2.1]octan-3-β-ol, temporarily protected on nitrogen by a protecting group PG such as the acid labile t-butyloxycarbonyl (Boc) group, with compounds of formula VI wherein n, Y, $Ar^1$ and $Ar^2$ have the meanings as previously defined. For example, the substitution reaction is effected using the Mitsunobu reaction with the aid of coupling reagents known in the art of organic chemistry, such as DEAD (diethylazodicarboxylate) and $PPh_3$ (triphenylphosphine), ADDP (1,1'-(azodicarbonyl)dipiperidine) and $PBu_3$ (tributylphosphine), or (4,4-Dimethyl-1,1-dioxido-1,2,5-thiadiazolidin-2-yl)triphenylphosphonium, in solvents such as THF, or DCM to afford N-protected 3-substituted-8-azabicyclo[3.2.1]octanes of formula VII. Treatment of compounds of formula VII with suitable reagents to remove the protecting group, such as trifluoroacetic acid to remove the t-butyloxycarbonyl (Boc) group, gives 3-substituted-8-azabicyclo[3.2.1]octanes of formula V (Scheme 2).

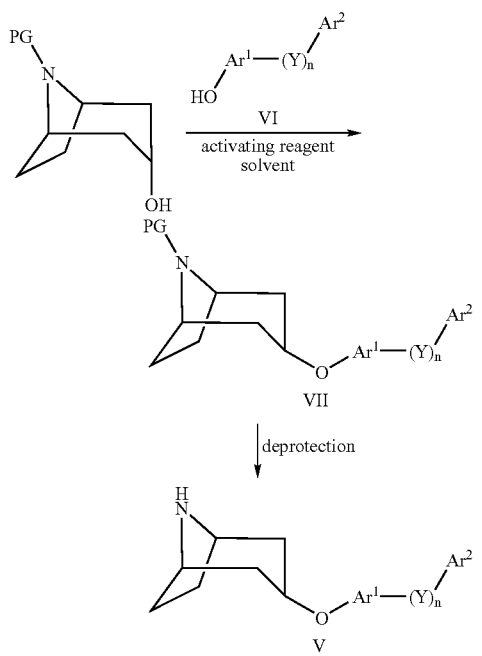

Alternatively, compounds of general formula VII are prepared by displacement of a leaving group from a 3-substituted-8-azabicyclo[3.2.1]octane VIII, where LG is a suitable leaving group, and PG is a suitable protecting group such as the acid labile t-butyloxycarbonyl (Boc) group, with compounds of formula VI using a suitable base such as sodium hydride, in a solvent such as DMF. Suitable leaving groups are, for example, a halide or an alkyl or aryl sulphonate (Scheme 3).

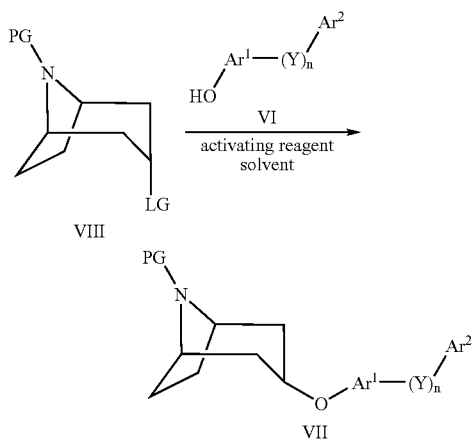

Alternatively, it will be readily appreciated by one skilled in the art that the compounds of general formula VII may be prepared by a nucleophilic aromatic substitution reaction involving displacement of a halogen, for example fluorine, from a compound such as IX, wherein n, Y, $Ar^1$ and $Ar^2$ have the meanings as previously defined and Hal is a halogen, with the alkoxide of 8-azabicyclo[3.2.1]octan-3-α-ol or 8-azabicyclo[3.2.1]octan-3-β-ol temporarily protected on nitrogen by a protecting group PG. Suitable bases for the formation of the alkoxide include, for example, sodium hydride in a solvent such as DMF (Scheme 4).

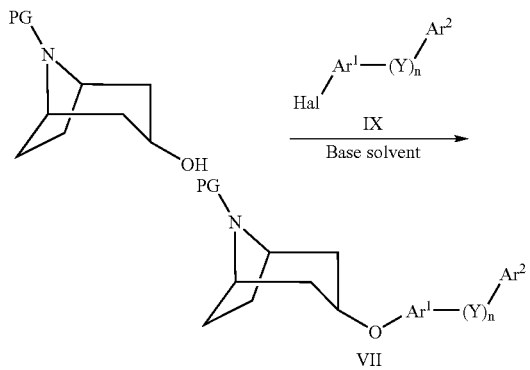

Compounds of general formula VI wherein n Y, $Ar^1$ and $Ar^2$ have the meanings as previously defined, are obtained from commercial sources, or are prepared by literature procedures or modifications of literature procedures known to persons skilled in the art. For example, in the case where n is 0, compounds of general formula XI are prepared by Suzuki reaction of a suitable aryl or heteroaryl boronic acid X with a suitable aryl or heteroaryl halide or triflate (a) Scheme 5, wherein Q is a halide or triflate. Furthermore, it will be readily appreciated by one skilled in the art that the compounds of general formula XI are also prepared using the opposite coupling partners, for example (b) Scheme 5. Alternatively compounds of general formula VI may be prepared by a variety of metal catalyzed Carbon-Carbon bond forming reactions well known to those skilled in the art—see for example Ei-ichi Negishi (Editor), Armin de Meijere (Associate Editor) *Handbook of Organopalladium Chemistry for Organic Synthesis*, John Wiley and Sons, 2002.

Scheme 5

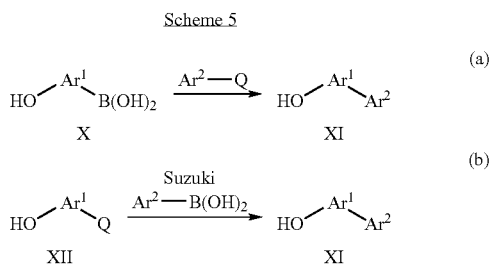

Compounds of general formula VI, wherein n is 1 and Y is O, are prepared from a boronic acid XIII wherein PG is a suitable protecting group such as a methyl ether, with a suitable nucleophile $Ar^2$—OH, wherein $Ar^2$ has the meaning previously defined, using methods previously described in the literature (Steven V. Ley, Andrew W. Thomas, *Angewandte Chemie International Edition*, 2003, Volume 42, Issue 44, 5400-5449). Treatment of compounds of formula XIV with suitable reagents to remove the protecting group, such as pyridine hydrochloride or boron tribromide to deprotect the methyl ether, gives compounds of formula VI, wherein Y is O and n is 1 (Scheme 6). Furthermore, it will be readily appreciated by one skilled in the art that the compounds of general formula VI can also be prepared using the opposite coupling partners, for example (b) Scheme 6

Scheme 6

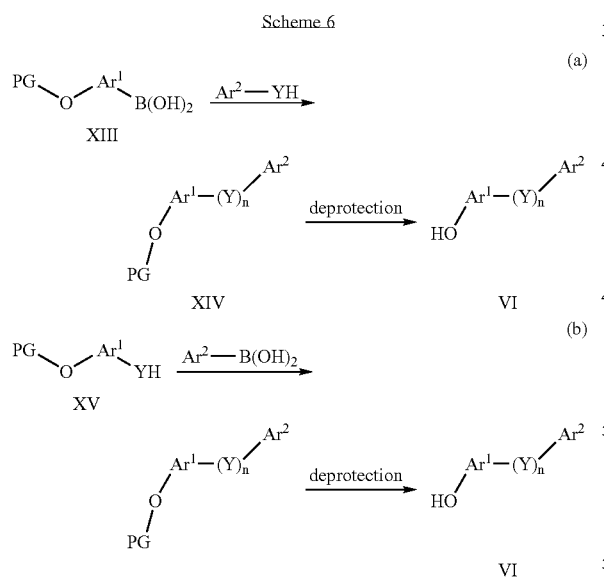

Alternatively, compounds of general formula VI, wherein n is 1 can be prepared by Ullmann coupling of a suitable nucleophile such as phenol and a suitable aryl or heteroaryl of formula XVI wherein Q is halide or triflate, temporarily protected by a protecting group PG. Suitable catalysts include CuBr with a base such as cesium carbonate in a suitable polar aprotic solvent such as DMF (a) Scheme 7. It will be readily appreciated that the compounds of general formula VI may also be prepared by a nucleophilic aromatic substitution reaction of a suitable nucleophile such as phenol with a suitable electrophile such as formula XVI wherein Q is a halogen, preferably fluoro, temporarily protected by a protecting group PG. Suitable bases include sodium hydride, in a polar aprotic solvent such as DMF. Furthermore, one skilled in the art will readily appreciate that compounds of the general formula VI are also prepared using the opposite coupling partners for example (b) Scheme 7, wherein n, Y, $Ar^1$, $Ar^2$, PG and Q have the meanings previously defined.

Scheme 7

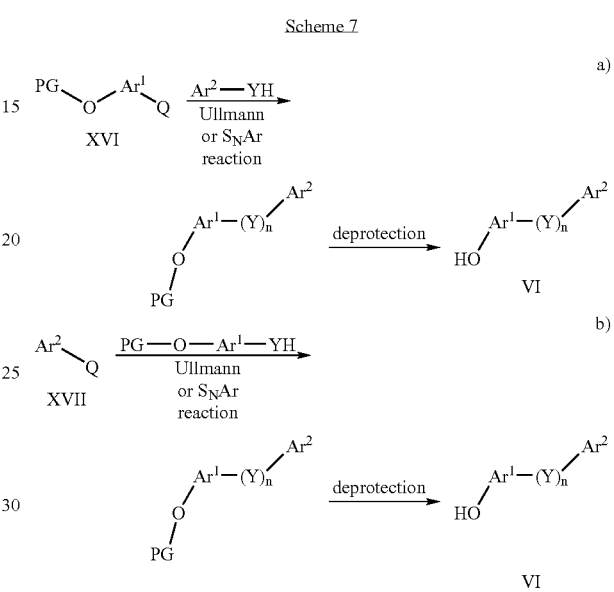

Compounds of general formula X, XII, XIII, XV, XVI and XVII are obtained from commerical sources, or are prepared by literature procedures or modifications of literature procedures known to persons skilled in the art. For example, by electrophillic aromatic substitution such as bromination with bromine or N-bromosuccinimide; chlorination with, for example, N-chlorosuccinimide and trifluoroacetic acid in a solvent such as DCM; diazotisation and then hydrolysis of commercially available aniline precursors using sodium nitrite and conc. sulphuric acid, or cyanation for example using zinc (II) cyanide with a suitable catalyst such as tetrakis (triphenylphosphine)palladium (0) in a suitable solvent such as DMF. See for example Leo Paquette, Editor-in-Chief, *Encyclopedia of Reagents for Organic Synthesis*, John Wiley and Sons, 1995.

It will be readily appreciated by one skilled in the art that the compounds of general formula I can be prepared using the general procedures and/or reaction sequences described above in any suitable order. For example, whereas the processes detailed above describe coupling of the $Ar^1$-Q and $(HO)_2B$—$Ar^2$ groups prior to Mitsunobu coupling, it will be recognized that, in some cases, the $Ar^1$-Q and $(OH)_2B$—$Ar^2$ or the $Ar^1$—$B(OH)_2$ and $Ar^2$-Q groups, can be coupled after the substitution reaction with 8-azabicyclo[3.2.1]octan-3-α-ol.

The present invention also includes within its scope all stereoisomeric forms of a 8-azabicyclo[3.2.1]octane derivative as disclosed herein. In particular, the invention includes both exo and endo stereoisomers resulting when the 3-substituent is in the exo and endo configuration respectively. In the case of individual stereoisomers of compounds of formula I or salts or solvates thereof, the present invention includes the aforementioned stereoisomer substantially free, i.e., associated with less than 5%, preferably less than 2% and in particular less than 1% of the other stereoisomer. Mixtures of stereoisomers in any proportions are also included within the scope of the present invention.

The present invention also includes within its scope all isotopically labelled forms of the 8-azabicyclo[3.2.1]octane derivatives disclosed herein. For example, compounds isotopically labelled with $^2$H, $^3$H, $^{11}$C, $^{13}$C, $^{14}$C, $^{131}$I, $^{125}$I, $^{123}$I and $^{18}$F. The labelled compounds are useful as diagnostic tools, radio tracers, or monitoring agents in various diagnostic methods and for in vivo receptor imaging.

The present invention also includes within its scope the 8-azabicyclo[3.2.1]octane derivatives of the present invention in the form as a free base and in the form of a pharmaceutically acceptable salt. These salts are also obtained by treatment of said free base with an organic or inorganic acid such as hydrogen chloride, hydrogen bromide, hydrogen iodide, sulfuric acid, phosphoric acid, acetic acid, trifluoroacetic acid, propionic acid, glycolic acid, maleic acid, malonic acid, methanesulphonic acid, fumaric acid, succinic acid, tartaric acid, citric acid, benzoic acid and ascorbic acid. All salts, whether pharmaceutically acceptable or not are included within the scope of the present invention.

The 8-azabicyclo[3.2.1]octane derivatives of the present invention exist in both solvated and unsolvated forms, including hydrated forms. Both these forms are encompassed within the scope of the present invention.

The 8-azabicyclo[3.2.1]octane derivatives of the present invention also exist as amorphous forms. Multiple crystalline forms are also possible. All these physical forms are included within the scope of the present invention.

The 8-azabicyclo[3.2.1]octane derivatives of the present invention are, inter alia, neurotransmitter reuptake inhibitors as demonstrated in vitro by their ability to inhibit the reuptake of one or more of serotonin, noradrenaline and dopamine in cells stably transfected with the human serotonin, noradrenaline and dopamine transporters. Consequently, the 8-azabicyclo[3.2.1]octane derivatives of the present invention are useful in therapy. As such, the 8-azabicyclo[3.2.1]octane derivatives of the present invention are useful in the manufacture of a medicament for the treatment or prevention of diseases for which the reuptake inhibition of one or more monoamines contributes to the therapeutic effect. In a further embodiment, the 8-azabicyclo[3.2.1]octane derivatives of the present invention are useful for the manufacture of a medicament for the treatment or prevention of a disease or disorder of the nervous system, both centrally and peripherally which is responsive to monoamine neurotransmission reuptake.

In a further aspect the 8-azabicyclo[3.2.1]octane derivatives of the present invention are useful for the treatment or prevention of depression, anxiety, pain, panic disorders, attention deficit hyperactivity disorder (ADHD), or obsessive compulsive disorder. Depression states in the treatment of which the 8-azabicyclo[3.2.1]octane derivatives of the present invention and their pharmaceutically acceptable salts and solvates are particularly useful are those classified as mood disorders in the *Diagnostic and Statistical Manual of Mental Disorders, Fourth Edition—Text Revised,* American Psychiatric Association, Washington D.C. (2000), including mood episodes, depressive disorders, bipolar disorders and other mood disorders.

The present invention further includes a method for the treatment of a mammal, including a human, suffering from or liable to suffer from any of the aforementioned diseases or disorders, which method comprises administering an effective amount of a 8-azabicyclo[3.2.1]octane derivative of the present invention or a pharmaceutically acceptable salt or solvate thereof.

The amount of a 8-azabicyclo[3.2.1]octane derivative of the present invention or a pharmaceutically acceptable salt or solvate thereof, also referred to herein as the active ingredient, which is required to achieve a therapeutic effect will, of course, vary with the particular compound, the route of administration, the age and condition of the recipient, and the particular disorder or disease being treated.

A suitable daily dose for any of the above mentioned disorders will be in the range of 0.001 to 50 mg per kilogram body weight of the recipient (e.g. a human) per day, preferably in the range of 0.01 to 20 mg per kilogram body weight per day. The desired dose may be presented as multiple subdoses administered at appropriate intervals throughout the day.

Whilst it is possible for the active ingredient to be administered alone, it is preferable to present it as a pharmaceutical formulation. The present invention therefore also provides a pharmaceutical composition comprising a 8-azabicyclo[3.2.1]octane derivative according to the present invention in admixture with one or more pharmaceutically acceptable excipients, such as the ones described in Gennaro et. al., Remmington: The *Science and Practice of Pharmacy,* 20$^{th}$ Edition, Lippincott, Williams and Wilkins, 2000; see especially part 5: pharmaceutical manufacturing. Suitable excipients are described e.g., in the Handbook of Pharmaceutical Excipients, 2$^{nd}$ Edition; Editors A. Wade and P. J. Weller, American Pharmaceutical Association, Washington, The Pharmaceutical Press, London, 1994. Compositions include those suitable for oral, nasal, topical (including buccal, sublingual and transdermal), parenteral (including subcutaneous, intravenous and intramuscular) or rectal administration.

The mixtures of a 8-azabicyclo[3.2.1]octane derivative according to the present invention and one or more pharmaceutically acceptable excipient or excipients may be compressed into solid dosage units, such as tablets, or be processed into capsules or suppositories.

By means of pharmaceutically suitable liquids the compounds can also be applied as an injection preparation in the form of a solution, suspension, emulsion, or as a spray, e.g., a nasal or buccal spray. For making dosage units e.g., tablets, the use of conventional additives such as fillers, colorants, polymeric binders and the like is contemplated. In general, any pharmaceutically acceptable additive can be used. The 8-azabicyclo[3.2.1]octane derivatives of the present invention are also suitable for use in an implant, a patch, a gel or any other preparation for immediate and/or sustained release.

Suitable fillers with which the pharmaceutical compositions can be prepared and administered include lactose, starch, cellulose and derivatives thereof, and the like, or mixtures thereof used in suitable amounts.

The following Examples further illustrate the compounds of the present invention and methods for their synthesis. The following examples are put forth so as to provide those of ordinary skill in the art with disclosure and description of how compounds, compositions and methods herein are made and evaluated, and are intended to be purely exemplary of the invention and are not intended to limit the scope of what the inventors regard as their invention. Unless indicated otherwise, percent is percent by weight given the component and the total weight of the composition, temperature is in ° C. or is at ambient temperature, and pressure is at or near atmospheric. Commercial reagents were used without further purification.

Methods

General Chemical Procedures. All reagents were either purchased from common commercial sources or synthesised according to literature procedures using commercial sources. Mass spectra were recorded on a Shimadzu LC-8A (HPLC) PE Sciex API 150EX LCMS. Analytical reversed-phase LCMS analysis was carried out on LUNA C18 column (5μ; 30×4.6 mm) under gradient conditions (90% water/0.1% formic acid to 90% acetonitrile/0.1% formic acid) at a flow rate of 4 mL/min. SCX (strong cation exchange) cartridges were purchased from Phenomenex.

Abbreviations

Dimethylformamide (DMF), dichloromethane (DCM), dimethylsulfoxide (DMSO), tetrahydrofuran (THF), high pressure liquid chromatography (HPLC), diisopropylethylamine (DIPEA), triethylamine (TEA), trifluoroacetic acid (TFA), tert-butyloxycarbonyl (Boc), ethylene glycol dimethyl ether (DME), dimethylacetamide (DMA) preparative LCMS refers to preparative high pressure liquid chromatography with mass spectrometric detection.

In the following section, examples of the synthesis of precursors and common intermediates for compounds of the present invention are described.

(4,4-Dimethyl-1,1-dioxido-1,2,5-thiadiazolidin-2-yl)triphenylphosphonium

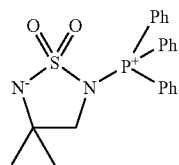

(4,4-Dimethyl-1,1-dioxido-1,2,5-thiadiazolidin-2-yl)triphenylphosphonium was prepared as described in *J. Org. Chem.*, 1994, 59, 2289-2291

3-endo-Hydroxy-8-azabicyclo[3.2.1]octane-8-carboxylic acid tert-butyl ester

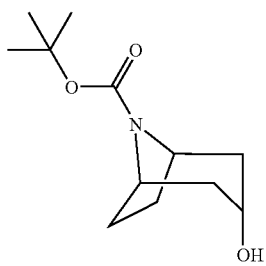

endo-8-Azabicyclo[3.2.1]octan-3-ol (3.6 g, 28.3 mmol) was dissolved in DCM (50 ml) and cooled to 0° C. Triethylamine (7.8 ml, 56.7 mmol) was added followed by addition of di-tert-butyl dicarbonate (7.4 g, 33.9 mmol). The reaction mixture was warmed to ambient temperature and stirred for 12 h. The reaction mixture was diluted with water. The organic layer was separated and washed with saturated citric acid (aq), water and brine. The organic layer was dried over MgSO$_4$ and concentrated in vacuo to afford 3-endo-hydroxy-8-azabicyclo[3.2.1]octane-8-carboxylic acid tert-butyl ester as a white solid (6.45 g, 28.4 mmol, 100%). M.S. (ESI) (m/z): 228 [M+H]$^+$ 3-exo-Hydroxy-8-azabicyclo[3.2.1]octane-8-carboxylic acid tert-butyl ester

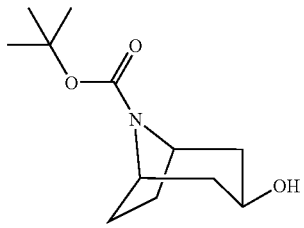

Diethylazodicarboxylate (1.74 mL, 11 mmol) was added dropwise to a solution of 3-endo-hydroxy-8-azabicyclo [3.2.1]octane-8-carboxylic acid tert-butyl ester (2.09 g, 9.2 mmol), triphenylphosphine (2.89 g, 11 mmol) and 4-nitrobenzoic acid (1.69 g, 10 mmol) in THF (25 mL). The reaction mixture was stirred under a nitrogen atmosphere for 18 h at ambient temperature. Volatiles were removed under reduced pressure and the residue was purified by chromatography on silica gel. Elution with DCM afforded the ester as a pale yellow solid (2.6 g, 6.9 mmol, 75%). 4N sodium hydroxide (aq) (3.6 mL, 14 mmol) was added to a solution of the ester in THF (25 mL) and the reaction mixture stirred at ambient temperature for 3 days. Diethyl ether (35 mL) and water (10 mL) were added to the reaction mixture. 2N sodium hydroxide (aq) solution was added to the organic layer which was removed, dried over Na$_2$SO$_4$ and the solvent evaporated in vacuo. The crude material was purified by chromatography on silica gel. Elution with DCM with a gradient to 5:95 methanol:DCM afforded 3-exo-hydroxy-8-azabicyclo[3.2.1] octane-8-carboxylic acid tert-butyl ester (1.4 g, 6.2 mmol, 89%) M.S. (ESI) (m/z): 228[M+H]$^+$ 3-exo-Methanesulfonyloxy-8-azabicyclo[3.2.1]octane-8-carboxylic acid tert-butyl ester

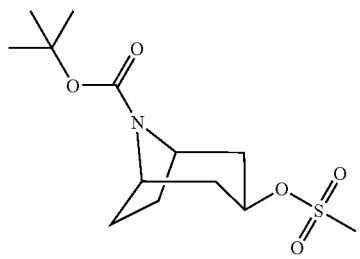

A solution of 3-exo-hydroxy-8-azabicyclo[3.2.1]octane-8-carboxylic acid tert-butyl ester (230 mg, 1.0 mmol) and triethylamine (0.148 mL, 1.1 mmol) in DCM (4 mL) was stirred under a nitrogen atmosphere and cooled to 0° C. Methanesulfonyl chloride (0.082 mL, 1.1 mmol) was added dropwise to the reaction mixture, which was allowed to rise to ambient temperature. The reaction mixture was stirred for a further 18 h. The reaction mixture was evaporated in vacuo and the residue purified by chromatography on silica gel. Elution with DCM with a gradient to 2:98 acetone:DCM afforded 3-exo-methanesulfonyloxy-8-azabicyclo[3.2.1]octane-8-carboxylic acid tert-butyl ester (298 mg, 0.98 mmol, 97%).

3-endo-Methanesulfonyloxy-8-azabicyclo[3.2.1]octane-8-carboxylic acid tert-butyl ester

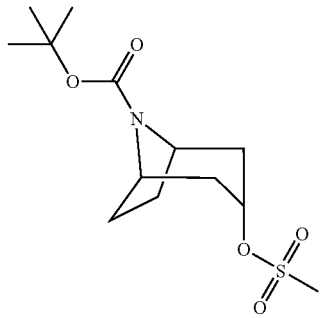

A solution of 3-endo-hydroxy-8-azabicyclo[3.2.1]octane-8-carboxylic acid tert-butyl ester (5.0 g, 22 mmol) and triethylamine (3.3 mL, 24 mmol) in dry DCM (40 mL) was stirred under an argon atmosphere and cooled to 0° C. Methane sulfonyl chloride (1.85 mL, 24 mmol) was added dropwise to the reaction mixture, which was allowed to warm to ambient temperature. The reaction mixture was stirred for a further 18 h, and the reaction mixture quenched by the addition of water. The organic layer was separated, dried over Na$_2$SO$_4$, absorbed onto silica gel and purified by chromatography on silica gel. Elution with 1:4 ethyl acetate:heptane afforded 3-endo-methanesulfonyloxy-8-azabicyclo[3.2.1]octane-8-carboxylic acid tert-butyl ester (4.0 g, 13 mmol, 60%).

4-Bromo-3-phenoxyphenol and 2,4-Dibromo-5-phenoxyphenol

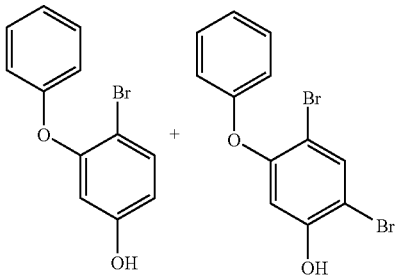

3-Phenoxyphenol (700 mg, 3.8 mmol) was stirred at 0° C. in DCM (7 mL) and bromine (0.154 mL, 3.0 mmol) was added dropwise. The reaction was stirred at ambient temperature for 10 min and then the solvents removed in vacuo to afford a crude oil which was purified by preparative HPLC to afford, in order of elution, 4-bromo-3-phenoxyphenol (126 mg, 0.5 mmol, 16%) M.S. (ESI) (m/z): 263,265 [M−H]$^-$; and 4,6-dibromo-3-phenoxyphenol (201 mg, 0.6 mmol, 39%) M.S. (ESI) (m/z): 341, 343, 345 [M−H]$^-$ Similarly prepared were:
6-Bromobiphenyl-3-ol
4-Bromobiphenyl-3-ol

4-Chloro-3-phenoxyphenol and 2-Chloro-5-phenoxyphenol

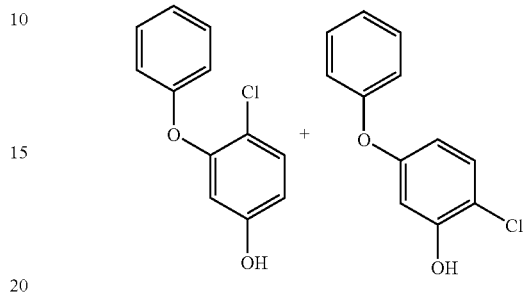

3-Phenoxyphenol (1.00 g, 5.4 mmol) was dissolved in MeCN (40 mL) and TFA (0.5 mL). N-Chlorosuccinimide (717 mg, 5.4 mmol) was added and the reaction stirred at ambient temperature for 48 h. Solvents were removed in vacuo to afford the crude product as an oil (2.15 g). 300 mg of this crude material was purified by HPLC to afford in order of elution 4-chloro-3-phenoxyphenol (68 mg, 0.31 mmol, 41%) M.S. (ESI) (m/z): 219,221 [M−H]$^-$; and 6-chloro-3-phenoxyphenol (73 mg, 0.33 mmol, 44%) M.S. (ESI) (m/z): 219,221 [M−H]$^-$.

Similarly prepared were:.
6-Chlorobiphenyl-3-ol
4-Chlorobiphenyl-3-ol

4-Chloro-3-(4-fluorophenoxy)phenol

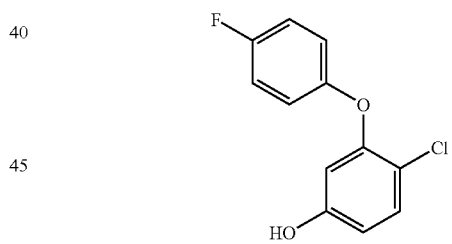

2-Bromo-1-chloro-4-methoxybenzene (200 mg, 0.9 mmol), cesium carbonate (588 mg, 1.8 mmol), 4-fluorophenol (202 mg, 1.8 mmol), CuI (17 mg, 0.09 mmol) and N-methylpyrrolidine (1 mL) were sealed in a microwave vessel and heated in a microwave at 200° C. for 1800 s. The crude reaction mixture was purified by chromatography on silica gel.

Elution with 10:90 ethyl acetate:heptane with a gradient to 30:70 ethyl acetate:heptane afforded 1-chloro-2-(4-fluorophenoxy)-4-methoxybenzene (112 mg, 0.44 mmol, 49%). 1-Chloro-2-(4-fluorophenoxy)-4-methoxybenzene (110 mg, 0.44 mmol) prepared above, was dissolved in DCM (5.00 mL) and stirred under argon at −78° C. Boron tribromide (1.0M in DCM, 2.20 mL) was then added and the reaction stirred at −78° C. for 1 h. The reaction was allowed to warm to ambient temperature overnight, quenched with saturated Na$_2$CO$_3$ (aq) and then the aqueous and organic layers were separated. The solvent was removed in vacuo and the crude product was purified by chromatography on silica gel. Elution with 2:98 ethyl acetate:heptane with a gradient to 20:80 ethyl acetate:heptane afforded 4-chloro-3-(4-fluorophenoxy)phenol (92 mg, 0.38 mmol, 87%). M.S. (ESI) (m/z): 237, 239 [M−H]⁻

5-Bromo-2-methylphenol

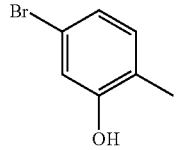

A solution of concentrated sulphuric acid (6 mL) in distilled water (75 mL) was added to 5-bromo-2-methylaniline (1 g, 5.38 mmol). The resultant suspension was heated to 90° C. and stirred for 4.5 h. The reaction mixture was then cooled using an ice bath and a solution of sodium nitrite (384 mg, 5.57 mmol) in water (5 mL) was added to the reaction mixture at 0° C. The reaction was then allowed to warm to ambient temperature. The reaction mixture was then added to a solution of concentrated sulphuric acid (6 mL) in water (75 mL) which had been preheated to 90° C. The reaction mixture was stirred for 1 h at 90° C. and allowed to cool, on standing, overnight. A precipitate was observed in the reaction mixture. The precipitate was collected by filtration, washed with water, and dried in a vacuum oven to afford 5-bromo-2-methylphenol as a brown solid (510 mg, 2.73 mmol, 51%). M.S. (ESI) (m/z) 185, 187[M−H]⁻

Similarly prepared were
3-Fluoro-5-iodophenol
5-Fluorobiphenyl-3-ol

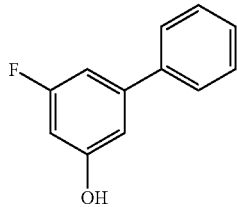

Palladium (II) acetate (2.4 mg, 0.01 mmol) was added to a suspension of 3-fluoro-5-iodophenol (250 mg, 1.05 mmol), phenylboronic acid (154 mg, 1.26 mmol) and sodium carbonate (3.34 g, 3.15 mmol) in water (5 mL), under an atmosphere of nitrogen. The reaction mixture was stirred at ambient temperature for 16 h. The reaction mixture was then filtered through a plug of dicalite to remove black precipitate. The dicalite was washed with MeOH. The filtrate was diluted with water (250 mL) and then adjusted to pH2 using 2M HCl (aq). The product was extracted into DCM, dried over Na₂SO₄ and concentrated in vacuo. The crude material was purified by chromatography on silica gel. Elution with 10:90 ethyl acetate:heptane afforded 5-fluorobiphenyl-3-ol (186 mg, 0.988 mmol, 94%) M.S. (ESI) (m/z): 187 [M−H]⁻.

Similarly prepared were:.
6-Fluorobiphenyl-3-ol
5-Bromobiphenyl-3-ol
1,1';3',1"Terphenyl-5'-ol
5-Chlorobiphenyl-3-ol
3-Thiophen-2-ylphenol 4-Phenylpyridin-2-ol

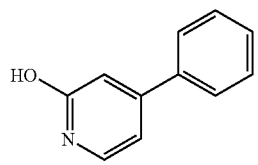

Tetrakis(triphenylphosphine)palladium (0) (164 mg, 0.14 mmol) was added to a stirred suspension of phenylboronic acid (345 mg, 2.84 mmol) and 4-bromo-2-hydroxypyridine (494 mg, 2.84 mmol) in DME (10 mL). The reaction mixture was stirred under an argon atmosphere for 90 min. Degassed 2N potassium carbonate solution (aq) (10 mL) was added and the reaction mixture stirred with heating at 90° C. for 72 h. The solvent was evaporated in vacuo, and the residue partitioned between ethyl acetate and water. The aqueous layer was washed with ethyl acetate (×2). The organics were combined, dried over Na₂SO₄ and the solvent evaporated in vacuo. The residue was purified by chromatography on silica gel. Elution with DCM with a gradient to 5:95 methanol:DCM afforded 4-phenylpyridin-2-ol (311 mg, 1.82 mmol, 64%) M.S. (ESI) (m/z): 172 [M+H]⁺.

Similarly prepared were:.
2-Phenylpyridin-4-ol
6-Phenylpyridin-2-ol
2'-Chlorobiphenyl-3-ol
3'-Chlorobiphenyl-3-ol
4'-Chlorobiphenyl-3-ol
4'-Trifluoromethylbiphenyl-3-ol
3'-Trifluoromethoxybiphenyl-3-ol
4'-Trifluoromethoxybiphenyl-3-ol
2'-Methylbiphenyl-3-ol
3'-Methylbiphenyl-3-ol
3'-Hydroxybiphenyl-2-carbonitrile
3'-Hydroxybiphenyl-4-carbonitrile
2'-Fluorobiphenyl-3-ol
3'-Fluorobiphenyl-3-ol
2'-Trifluoromethylbiphenyl-3-ol
3'-Hydroxybiphenyl-3-carbonitrile
3-Pyridin-3-ylphenol
4-Chlorobiphenyl-3-ol
3'-Methoxybiphenyl-3-ol
2'-Fluorobiphenyl-3-ol
3'-Trifluoromethylbiphenyl-3-ol
4'-Methoxybiphenyl-3-ol
2'-Trifluoromethylbiphenyl-3-ol
2'-Methoxybiphenyl-3-ol
3'-Methoxybiphenyl-3-ol
3'-Hydroxybiphenyl-3-carbonitrile

5-Hydroxybiphenyl-3-carbonitrile

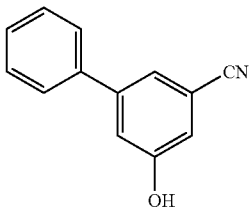

Tetrakis(triphenylphosphine)palladium (0) (116 mg, 0.1 mmol) was added to 5-bromobiphenyl-3-ol (250 mg, 1 mmol) and zinc cyanide (117 mg, 1.0 mmol) dissolved in DMF (5 mL) in a microwave vessel. The reaction vessel was sealed and then heated at 200° C. for 300 seconds. The reaction was quenched with water and the product was extracted into DCM. The solution was filtered and then concentrated in vacuo. The crude material was then purified by chromatography on silica gel. Elution with 10:90 ethyl acetate:heptane afforded 5-hydroxybiphenyl-3-carbonitrile (74 mg, 0.379 mmol, 38%). M.S. (ESI) (m/z): 194 [M−H]⁻.

Similarly prepared were:
5-Hydroxybiphenyl-2-carbonitrile

2-Methyl-3-phenoxyphenol

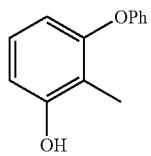

1-Bromo-3-fluoro-2-methylbenzene (388 mg, 2.05 mmol), and (4-methoxyphenyl)methanol (0.511 mL, 4 mmol) were dissolved in DMF (5 mL) in a microwave vessel. Sodium hydride as a 60% dispersion in mineral oil (164 mg, 4.0 mmol) was added portionwise under a flow of nitrogen over 10 min. The reaction vessel was then sealed and heated at 180° C. for 900s. The crude reaction mixture was poured onto 1:1 water:brine (6 mL) and DCM (10 mL). The biphasic mixture was stirred at ambient temperature for 1 h and then the organic and aqueous layers were separated. The combined organics were dried over Na₂SO₄ and concentrated in vacuo. The crude material was then purified by chromatography on silica gel. Elution with 5:95 ethyl acetate:heptane afforded 1-bromo-3-(4-methoxybenzyloxy)-2-methylbenzene (289 mg, 0.9 mmol, 46%).

Sodium hydride as a 60% dispersion in mineral oil (56 mg, 1.4 mmol) was added portionwise to a solution of phenol (0.35M in DMF, 2 mL). The resultant solution was added to a mixture of 1-bromo-3-(4-methoxybenzyloxy)-2-methylbenzene (215 mg, 0.7 mmol) and cesium carbonate (228 mg, 0.7 mmol) in a microwave vessel. Copper (I) bromide (10 mg) was added, the vessel was sealed and the reaction heated at 180° C. for 900 s. 1N NaOH (aq) (2 mL) and DCM (5 mL) were added to the cooled reaction mixture and the organic layer was separated and concentrated in vacuo. The crude material was then purified by chromatography on silica gel. Elution with 5:95 ethyl acetate:heptane afforded 1-(4-methoxybenzyloxy)-2-methyl-3-phenoxybenzene (205 mg, 0.64 mmol, 91%).

1-(4-Methoxybenzyloxy)-2-methyl-3-phenoxybenzene (205 mg, 0.64 mmol) was dissolved in ethanol (5 mL) and palladium on charcoal 10% wt (60 mg) was added. The reaction mixture was agitated under an atmosphere of hydrogen (1 atm) for 72 h. The crude reaction mixture was filtered over dicalite and the solvents removed in vacuo. The crude product was taken up in DCM (4 mL) and 1N NaOH (aq) (4 mL) and the aqueous layer was separated, then acidified to pH 1 with 5N HCl (aq). The aqueous layer was extracted with DCM (10 mL) and the combined organics were concentrated in vacuo. The crude material was then purified by chromatography on silica gel. Elution with 5:95 ethyl acetate:heptane afforded 2-methyl-3-phenoxyphenol (43 mg, 0.21 mmol, 34%).

Similarly prepared were:.
2,3-Dimethyl-5-phenoxyphenol
3-Phenoxy-4-trifluoromethylphenol
3-Phenoxy-5-trifluoromethylphenol
4-Methyl-3-phenoxyphenol
2-Fluoro-3-methoxy-5-phenoxyphenol

5-Phenylpyridin-3-ol

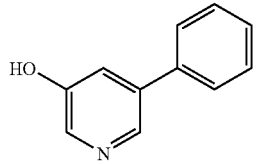

Tetrakis(triphenylphosphine)palladium(0) (242 mg, 0.21 mmol) was added to a stirred solution of phenyl boronic acid (510 mg, 4.18 mmol) and 3-bromo-5-methoxypyridine (786 mg, 4.18 mmol) in DME (10 mL). The reaction mixture was stirred under an argon atmosphere for 30 min. Degassed potassium carbonate (aq) (10 mL) was added and the reaction mixture stirred with heating at 90° C. for 18 h. The solvent was evaporated in vacuo, and the residue partitioned between ethyl acetate and water. The aqueous layer was washed with ethyl acetate. The organics were combined, dried over Na₂SO₄ and the solvent evaporated in vacuo. The residue was purified by chromatography on silica gel. Elution with 10:90 ethyl acetate:isohexane with a gradient to 15:85 ethyl acetate: isohexane afforded a yellow oil. The oil was dissolved in DCM, and cooled to −78° C. under a nitrogen atmosphere. Boron tribromide (1.0M in DCM, 9.15 mL) was added dropwise over 20 min and the reaction mixture was warmed to ambient temperature and stirred at this temperature for 18 h. The resultant mixture was basified to pH8 by the dropwise addition of saturated sodium hydrogen carbonate (aq). The organics were removed and the aqueous residue extracted into ethyl acetate (×3). The organic layers were combined, dried over Na₂SO₄ and evaporated in vacuo to give 5-phenylpyridin-3-ol (245 mg, 1.43 mmol, 47%) M.S. (ESI) (m/z): 172 [M+H]⁺.

Similarly prepared were:
2-Fluorobiphenyl-3-ol
2'-Fluoro-3'-hydroxybiphenyl-4-carbonitrile 2,4-Dichloro-6-hydroxypyridine

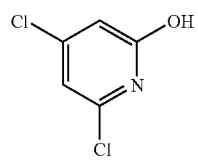

Sodium nitrite (64 mg, 0.93 mmol) dissolved in water (0.6 mL), was added dropwise to a stirred solution of 2-amino-4,6-dichloropyridine (prepared according to the method described in *Recl. Trav. Chim. Pays-Bas,* 1950, 69, 673) (126 mg, 0.77 mmol) in 5% sulphuric acid (aq) (5 mL) at 0° C., over 5 min. The mixture was stirred at 0° C. for 1 h and then diluted with water (20 mL) and extracted with DCM (3×20 mL). The combined extracts were washed with brine (20 mL), dried over MgSO$_4$ and concentrated in vacuo to afford the 2,4-dichloro-6-hydroxypyridine (116 mg, 0.71 mmol, 92%) M.S. (ESI) (m/z) 164,166 [M+H]$^+$.

The present invention is further illustrated by the following examples:

Procedure I

EXAMPLE I.1

3-exo-(3-Phenoxyphenoxy)-8-azabicyclo[3.2.1]octane

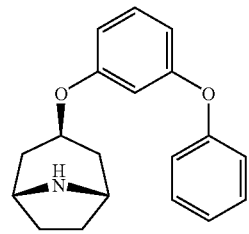

Diethylazodicarboxylate (1.89 mL, 12 mmol) was added dropwise to a solution of 3-endo-hydroxy-8-azabicyclo[3.2.1]octane-8-carboxylic acid tert-butyl ester (2.27 g, 10 mmol), triphenylphosphine (3.15 g, 12 mmol) and 3-phenoxyphenol (1.93 mL, 12 mmol) in THF (60 mL). The reaction mixture was stirred under a nitrogen atmosphere for 72 h at ambient temperature. Volatiles were removed under reduced pressure. The resultant material was dissolved in DCM (50 mL) and TFA (5 mL) added. The reaction mixture was stirred at ambient temperature for 12 h. Volatiles were removed under reduced pressure, the crude product dissolved in methanol (40 mL) and the solution loaded onto a SCX cartridge (20 g). The cartridge was eluted with methanol (40 mL) to remove triphenylphosphine oxide. Elution with ammonia in methanol (2M, 40 mL) followed by evaporation in vacuo afforded crude 3-(3-phenoxyphenoxy)-8-azabicyclo[3.2.1]octane as an oil. The crude material was then purified by chromatography on silica gel. Elution with 98:2 DCM:MeOH with a gradient to 90:10:0.5 DCM:MeOH:ammonia, afforded the product as an oil. The product was dissolved in methanol (5 mL) and treated with hydrochloric acid in methanol until the solution was acidic. The solution was concentrated in vacuo and diethyl ether was added to precipitate the product. The precipitate was collected by filtration and recrystallised from methanol/diethyl ether to afford 3-exo-(3-phenoxyphenoxy)-8-azabicyclo[3.2.1]octane as the hydrochoride salt (1.08 g, 3.26 mmol, 33%). M.S. (ESI) (m/z): 296 [M+H]$^+$.

Similarly prepared were

EXAMPLE I.2

3-exo-(4-Chloro-3-(4-fluorophenoxy)phenoxy)-8-azabicyclo[3.2.1]octane

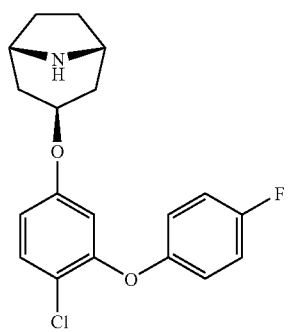

M.S. (ESI) (m/z): 348, 350 [M+H]$^+$.

EXAMPLE I.3

3-exo -(5-Chlorobiphenyl-3-yloxy)-8-azabicyclo[3.2.1]octane

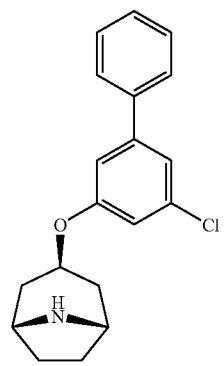

MS (ESI) (m/z): 314, 316 [M+H]$^+$.

EXAMPLE I.4

3-exo-(5-Bromobiphenyl-3-yloxy)-8-azabicyclo[3.2.1]octane

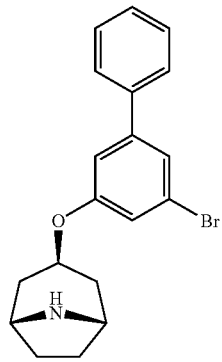

M.S. (ESI) (m/z): 358, 360 [M+H]$^+$.

EXAMPLE I.5 exo 5-(8-Azabicyclo[3.2.1]oct-3-yloxy)biphenyl-3-carbonitrile

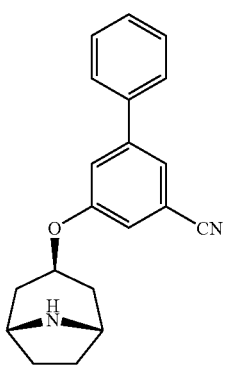

MS (ESI) (m/z): 305 [M+H]$^+$.

EXAMPLE I.6

3-exo-([1,1';3',1'']Terphenyl-5'-yloxy)-8-azabicyclo[3.2.1]octane

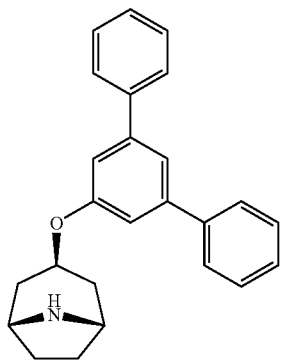

M.S. (ESI) (m/z): 356 [M+H]$^+$.

EXAMPLE I.7

3-exo-(5-Fluorobiphenyl-3-yloxy)-8-azabicyclo[3.2.1]octane

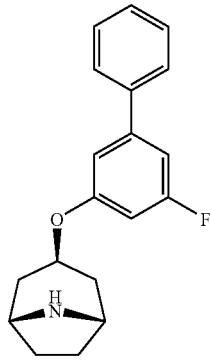

M.S. (ESI) (m/z): 298 [M+H]$^+$.

EXAMPLE I.8

3-exo-(6-Fluorobiphenyl-3-yloxy)-8-azabicyclo[3.2.1]octane

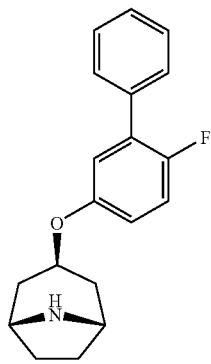

M.S. (ESI) (m/z): 298 [M+H]$^+$.

EXAMPLE I.9

3-exo-(Biphenyl-3-yloxy)-8-azabicyclo[3.2.1]octane

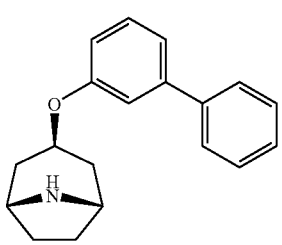

M.S. (ESI) (m/z): 280 [M+H]$^+$.

EXAMPLE I.10

3-exo-(6-Chlorobiphenyl-3-yloxy)-8-azabicyclo[3.2.1]octane

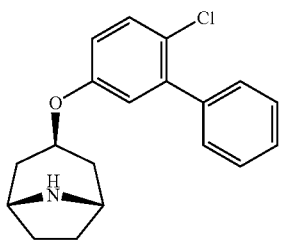

M.S. (ESI) (m/z): 314,316 [M+H]+.

EXAMPLE I.11

3-exo-(4-Chloro-3-phenoxyphenoxy)-8-azabicyclo[3.2.1]octane

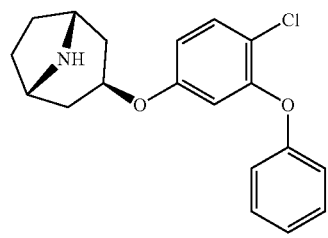

M.S. (ESI) (m/z): 330,332 [M+H]+.

EXAMPLE I.12

3-exo-(2-Chloro-5-phenoxyphenoxy)-8-azabicyclo[3.2.1]octane

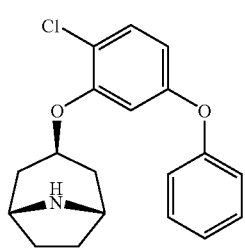

M.S. (ESI) (m/z): 330,332 [M+H]+.

EXAMPLE I.13

3-exo-(4-Bromobiphenyl-3-yloxy)-8-azabicyclo[3.2.1]octane

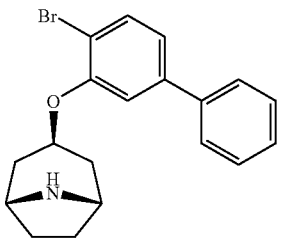

M.S. (ESI) (m/z): 358,360 [M+H]+.

EXAMPLE I.14

3-exo-(6-Bromobiphenyl-3-yloxy)-8-aza-bicyclo[3.2.1]octane

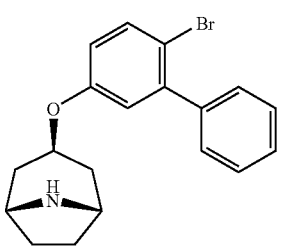

M.S. (ESI) (m/z): 358,360 [M+H]+.

EXAMPLE I.15

3-exo-(4-Bromo-3-phenoxyphenoxy)-8-azabicyclo[3.2.1]octane

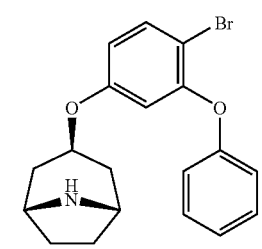

M.S. (ESI) (m/z): 374,376 [M+H]+.

EXAMPLE I.16 exo 5-(8-Azabicyclo[3.2.1]oct-3-yloxy)biphenyl-2-carbonitrile

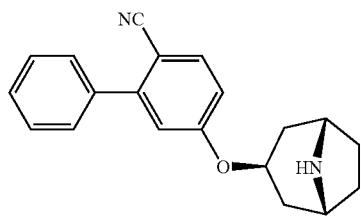

M.S. (ESI) (m/z): 305 [M+H]⁺.

EXAMPLE I.17

3-exo-(Dibenzofuran-2-yloxy)-8-azabicyclo[3.2.1]octane

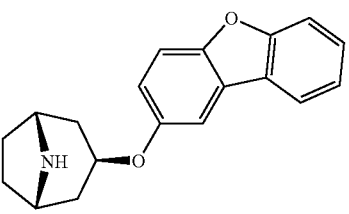

M.S. (ESI) (m/z): 294 [M+H]⁺.

EXAMPLE I.18

3-exo-(3-Phenethyloxyphenoxy)-8-azabicyclo[3.2.1]octane

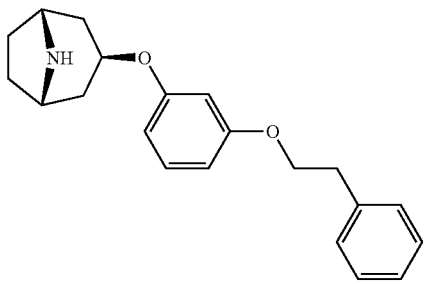

M.S. (ESI) (m/z): 324 [M+H]⁺.

EXAMPLE I.19

3-exo-(3-Thiophen-2-ylphenoxy)-8-azabicyclo[3.2.1]octane

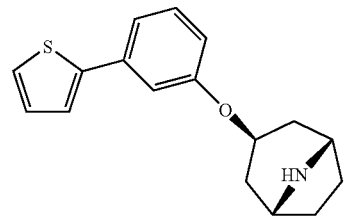

M.S. (ESI) (m/z): 286 [M+H]⁺.

Procedure II

EXAMPLE II.1

3-exo-(4-Fluoro-3-phenoxyphenoxy)-8-azabicyclo[3.2.1]octane

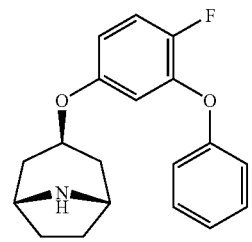

Diethylazodicarboxylate (1.65 mL, 10.5 mmol) was added dropwise to a solution of 3-endo-hydroxy-8-azabicyclo[3.2.1]octane-8-carboxylic acid tert-butyl ester (2.16 g, 9.5 mmol), triphenylphosphine (2.75 g, 10.5 mmol) and 4-fluoro-3-bromophenol (2.0 g, 10.5 mmol) in THF (95 mL). The reaction mixture was stirred under a nitrogen atmosphere for 72 h at ambient temperature. Volatiles were removed under reduced pressure, the residue was then triturated with 5:1 heptane:diethyl ether followed by filtration to remove precipitated triphenylphosphine oxide. The filtrate was concentrated in vacuo. The crude material was purified by chromatography on silica gel. Elution with 15:85 ethyl acetate:heptane, followed by washing with 1N NaOH (aq) (50 mL) then concentration in vacuo afforded 3-exo-(3-bromo-4-fluorophenoxy)-8-azabicyclo[3.2.1]octane-8-carboxylic acid tert-butyl ester (2.18 g, 5.5 mmol, 57%).

3-exo-(3-Bromo-4-fluorophenoxy)-8-azabicyclo[3.2.1]octane-8-carboxylic acid tert-butyl ester (150 mg, 0.37 mmol), cesium carbonate (244 mg, 0.75 mmol), phenol (70.5 mg, 0.75 mmol) and copper (I) iodide (7 mg, 0.04 mmol) were combined with N-methylpyrrolidine (1 mL) in a microwave vessel. The reaction was heated at 200° C. for 1800 s. TFA (1 mL) was then added and the reaction stirred at ambient temperature for 16 h. DCM (2 mL) was added followed by 1N NaOH (aq) to pH 10. The aqueous and organic layers were separated and the combined organics were concentrated in vacuo. The crude product was purified by preparative LCMS to afford 3-exo-(4-fluoro-3-phenoxyphenoxy)-8-azabicyclo

[3.2.1]octane as the trifluoroacetic acid salt (20.6 mg, 0.05 mmol, 13%) M.S. (ESI) (m/z): 314 [M+H]$^+$.

Similarly prepared were:

EXAMPLE II.2

3-exo-(3-(3-Chlorophenoxy)-4-fluorophenoxy)-8-azabicyclo[3.2.1]octane

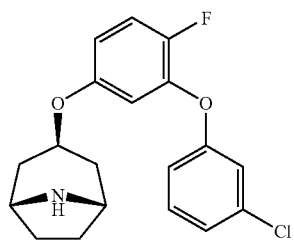

M.S. (ESI) (m/z): 348, 350 [M+H]$^+$.

EXAMPLE II.3

3-exo-(3-(3,4-Dichlorophenoxy)-4-fluorophenoxy)-8-azabicyclo[3.2.1]octane

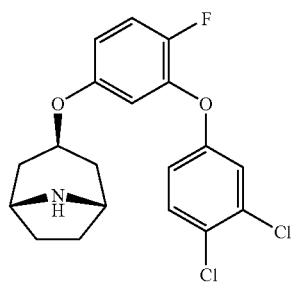

M.S. (ESI) (m/z): 382, 384 [M+H]$^+$.

EXAMPLE II.4

3-exo-(3-(4-Chlorophenoxy)-4-fluorophenoxy)-8-azabicyclo[3.2.1]octane

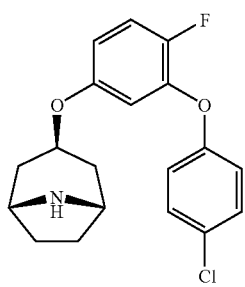

M.S. (ESI) (m/z): 348, 350 [M+H]$^+$.

EXAMPLE II.5

3-exo-(4-Fluoro-3-(3-methoxyphenoxy)phenoxy)-8-azabicyclo[3.2.1]octane

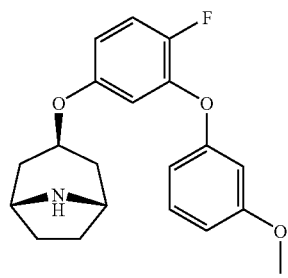

M.S. (ESI) (m/z): 344 [M+H]$^+$.

EXAMPLE II.6 exo 3-[5-(8-Azabicyclo[3.2.1]oct-3-yloxy)-2-fluorophenoxy]benzonitrile

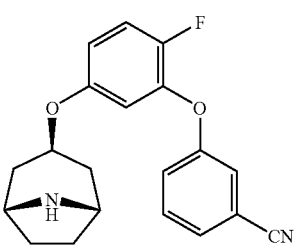

M.S. (ESI) (m/z): 339 [M+H]$^+$.

EXAMPLE II.7 exo 3-[3-(Pyridin-3-yloxy)phenoxy]-8-azabicyclo[3.2.1]octane

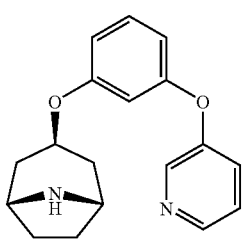

M.S. (ESI) (m/z): 297 [M+H]$^+$.

Procedure III

EXAMPLE III.1

3-exo-(6-Phenylpyridin-2-yloxy)-8-azabicyclo[3.2.1]octane

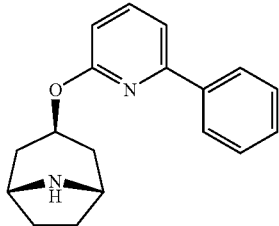

A solution of 6-phenylpyridin-2-ol (75 mg, 0.44 mmol) in DMF (2.5 mL) was added dropwise to a stirred suspension of sodium hydride (21 mg, 0.53 mmol) in DMF (0.5ml) in a microwave vessel. The resultant suspension was stirred under a nitrogen atmosphere for 30 min. 3-endo-methanesulfonyloxy-8-azabicyclo[3.2.1]octane-8-carboxylic acid tert-butyl ester (147 mg, 0.48 mmol) was added to the reaction mixture. The reaction vessel was sealed and then heated at 80° C. for 600 seconds then at 100° C. for 1200 seconds. The solvent was removed in vacuo and the residue partitioned between ethyl acetate and water. The aqueous layer was washed with ethyl acetate and the organics combined, dried over $Na_2SO_4$ and the solvent evaporated in vacuo. The residue was purified by chromatography on silica gel. Elution with DCM with a gradient to 1:99 methanol:DCM afforded a yellow gum. The crude material was dissolved in MeOH and the solution loaded onto a SCX cartridge (500 mg). The cartridge was eluted with methanol (15 mL) to remove unreacted starting material then with ammonia in methanol (2M, 7.5 mL) which was evaporated in vacuo. The resultant material was dissolved in DCM (1.5 mL) and TFA (0.5 mL) added. The reaction mixture was stirred at ambient temperature for 1 h. Volatiles were removed in vacuo, the crude material dissolved in methanol (3 mL) and the solution loaded onto a SCX cartridge (500 mg). The cartridge was eluted with methanol (15 mL) to remove impurities. Elution with ammonia in methanol (2M, 7.5 mL) followed by evaporation in vacuo afforded 3-exo-(6-phenylpyridin-2-yloxy)-8-azabicyclo[3.2.1]octane (17.1 mg, 0.25 mmol, 58%). M.S. (ESI) (m/z): 281 [M+H]$^+$.

Similarly prepared were

EXAMPLE III.2

3-exo-(2-Phenylpyridin-4-yloxy)-8-azabicyclo[3.2.1]octane

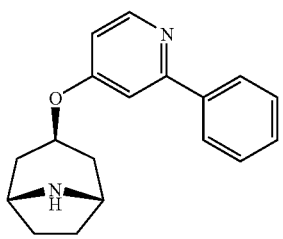

M.S. (ESI) (m/z): 281 [M+H]$^+$.

EXAMPLE III.3

3-exo-(4-Phenylpyridin-2-yloxy)-8-azabicyclo[3.2.1]octane

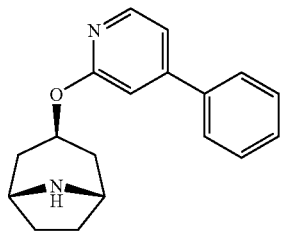

M.S. (ESI) (m/z): 281 [M+H]$^+$.

EXAMPLE III.4

3-exo-(3-Pyridin-3-ylphenoxy)-8-azabicyclo[3.2.1]octane

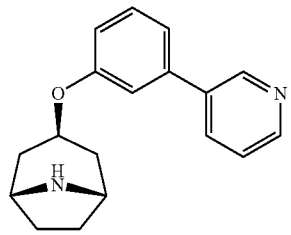

M.S. (ESI) (m/z): 281 [M+H]$^+$.

EXAMPLE III.5

3-endo-(3-Phenoxyphenoxy)-8-azabicyclo[3.2.1]octane

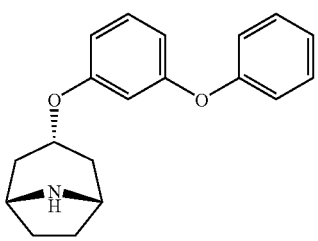

M.S. (ESI) (m/z): 296 [M+H]$^+$.

The title compound was prepared from 3-exo-methanesulfonyloxy-8-azabicyclo[3.2.1]octane-8-carboxylic acid tert-butyl ester

EXAMPLE III.6 exo 1-{3'-(8-Azabicyclo[3.2.1]oct-3-yloxy)biphenyl-4-yl}ethanone

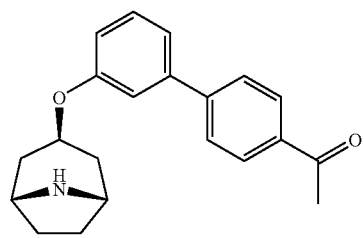

M.S. (ESI) (m/z): 322 [M+H]+.

Procedure IV

EXAMPLE IV.1

3-exo-(4'-Trifluoromethylbiphenyl-3-yloxy)-8-azabicyclo[3.2.1]octane

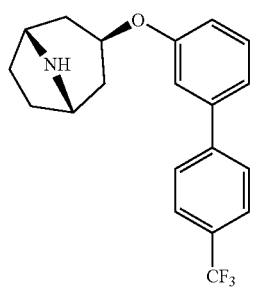

(4,4-Dimethyl-1,1-dioxido-1,2,5-thiadiazolidin-2-yl)triphenylphosphonium (172 mg, 0.420 mmol) was added to a solution of 3-endo-hydroxy-8-azabicyclo[3.2.1]octane-8-carboxylic acid tert-butyl ester (95 mg, 0.42 mmol), and 4'-trifluoromethylbiphenyl-3-ol (50 mg, 0.21 mmol) in THF (2 mL). The reaction mixture was stirred for 18 h at ambient temperature. Volatiles were removed under reduced pressure. The resultant material was dissolved in DCM (1 mL) and TFA (1 mL) was added. The reaction mixture was stirred at ambient temperature for 4 h. Volatiles were removed under reduced pressure, the crude product dissolved in methanol (2 mL) and the solution loaded onto a SCX cartridge (5 g). The cartridge was eluted with methanol (3×10 mL) to remove triphenylphosphine oxide. Elution with ammonia in methanol (2M, 10 mL) followed by evaporation in vacuo afforded crude 3-(4'-trifluoromethylbiphenyl-3-yloxy)-8-azabicyclo[3.2.1]octane as an oil. The crude material was then purified by preparative LCMS to afford 3-exo-(4'-trifluoromethylbiphenyl-3-yloxy)-8-azabicyclo[3.2.1]octane as the trifluoro acetic acid salt (36.9 mg, 0.080 mmol, 38%) M.S. (ESI) (m/z): 348 [M+H]+.

Similarly prepared were:

EXAMPLE IV.2

3-exo-(4-Chlorobiphenyl-3-yloxy)-8-azabicyclo[3.2.1]octane

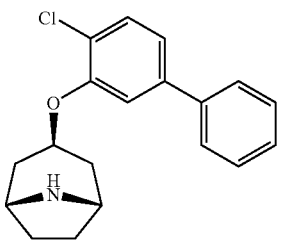

M.S. (ESI) (m/z): 314, 316 [M+H]+.

EXAMPLE IV.3

3-exo-(2'-Chlorobiphenyl-3-yloxy)-8-azabicyclo[3.2.1]octane

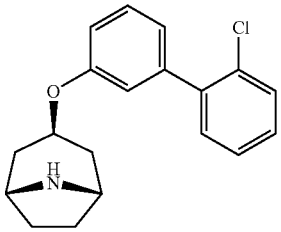

M.S. (ESI) (m/z): 314, 316 [M+H]+.

EXAMPLE IV.4

3-exo-(3'-Chlorobiphenyl-3-yloxy)-8-azabicyclo[3.2.1]octane

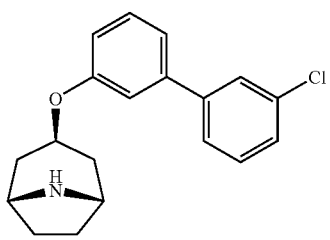

M.S. (ESI) (m/z): 314, 316 [M+H]+.

EXAMPLE IV.5

3-exo-(4'-chlorobiphenyl-3-yloxy)-8-azabicyclo[3.2.1]octane

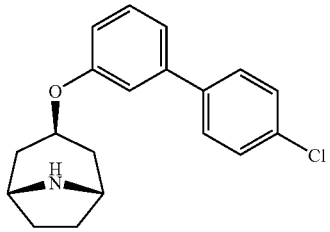

M.S. (ESI) (m/z): 314, 316 [M+H]$^+$.

EXAMPLE IV.6

3-exo-(2'-Fluorobiphenyl-3-yloxy)-8-azabicyclo[3.2.1]octane

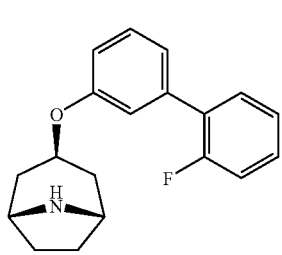

M.S. (ESI) (m/z): 298 [M+H]$^+$.

EXAMPLE IV.7

3-exo-(4'-Fluorobiphenyl-3-yloxy)-8-azabicyclo[3.2.1]octane

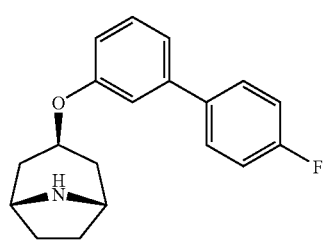

M.S. (ESI) (m/z): 298 [M+H]$^+$.

EXAMPLE IV.8

3-exo-(2'-Trifluoromethylbiphenyl-3-yloxy)-8-azabicyclo[3.2.1]octane

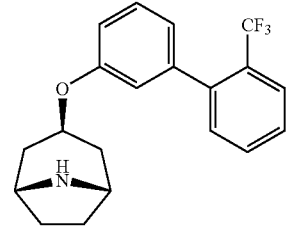

M.S. (ESI) (m/z): 348 [M+H]$^+$.

EXAMPLE IV.9

3-exo-(2-Fluoro-3-methoxy-5-phenoxyphenoxy)-8-azabicyclo[3.2.1]octane

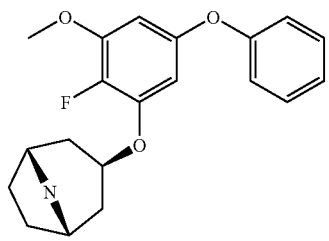

M.S. (ESI) (m/z): 344 [M+H]$^+$.

EXAMPLE IV.10

3-exo-(3'-Trifluoromethoxybiphenyl-3-yloxy)-8-azabicyclo[3.2.1]octane

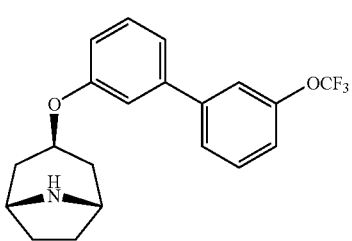

M.S. (ESI) (m/z): 364 [M+H]$^+$.

EXAMPLE IV.11

3-exo-(2'-Methylbiphenyl-3-yloxy)-8-azabicyclo[3.2.1]octane

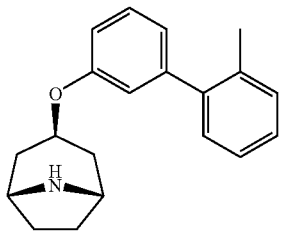

M.S. (ESI) (m/z): 294 [M+H]⁺.

EXAMPLE IV.12

3-exo-(3'-Methylbiphenyl-3-yloxy)-8-azabicyclo[3.2.1]octane

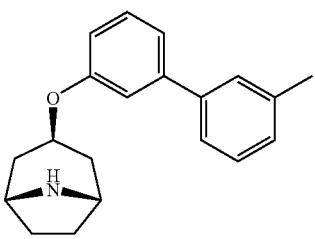

M.S. (ESI) (m/z): 294 [M+H]⁺.

EXAMPLE IV.13

3-exo-(3-Phenoxy-4-trifluoromethylphenoxy)-8-azabicyclo[3.2.1]octane

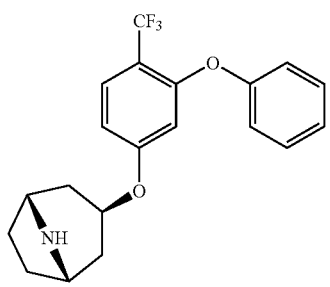

M.S. (ESI) (m/z): 364 [M+H]⁺.

EXAMPLE IV.14 exo 3'-(8-Azabicyclo[3.2.1]oct-3-yloxy)biphenyl-2-carbonitrile

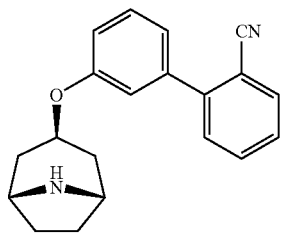

M.S. (ESI) (m/z): 305 [M+H]⁺.

EXAMPLE IV.15 exo 3'-(8-Azabicyclo[3.2.1]oct-3-yloxy)biphenyl-3-carbonitrile

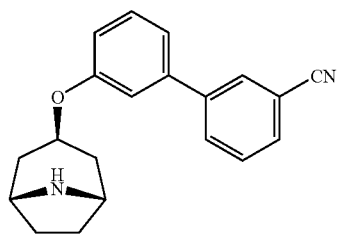

M.S. (ESI) (m/z): 305 [M+H]⁺.

EXAMPLE IV.16 exo 3'-(8-Azabicyclo3.2.1]oct-3-yloxy)biphenyl-4-carbonitrile

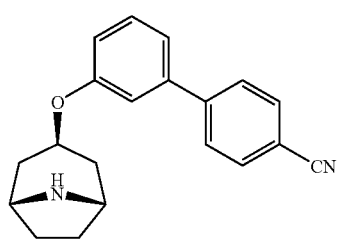

M.S. (ESI) (m/z): 305 [M+H]⁺.

EXAMPLE IV.17

3-exo-(3-Phenoxy-5-trifluoromethylphenoxy)-8-azabicyclo[3.2.1]octane

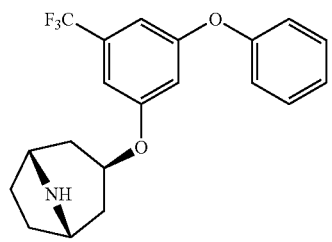

M.S. (ESI) (m/z): 364 [M+H]$^+$.

EXAMPLE IV.18

3-exo-(4-Methyl-3-phenoxyphenoxy)-8-azabicyclo[3.2.1]octane

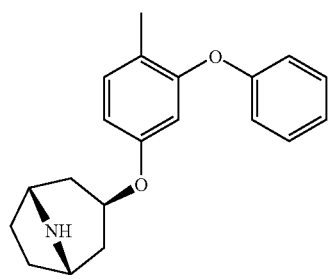

M.S. (ESI) (m/z): 310 [M+H]$^+$.

EXAMPLE IV.19

3-exo-(3-Chloro-5-phenoxyphenoxy)-8-azabicyclo[3.2.1]octane

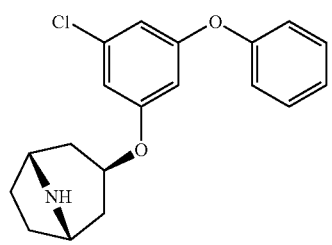

M.S. (ESI) (m/z): 330,332 [M+H]$^+$.

EXAMPLE IV.20 exo 3-(8-Azabicyclo[3.2.1]oct-3-yloxy)-5-phenoxy-benzonitrile

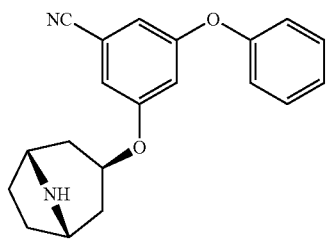

M.S. (ESI) (m/z): 321 [M+H]$^+$.

EXAMPLE IV.21

3-exo-(3'-Fluorobiphenyl-3-yloxy)-8-azabicyclo[3.2.1]octane

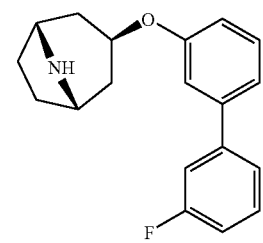

M.S. (ESI) (m/z): 298 [M+H]$^+$.

EXAMPLE IV.22

3-exo-(3'-Trifluoromethylbiphenyl-3-yloxy)-8-azabicyclo[3.2.1]octane

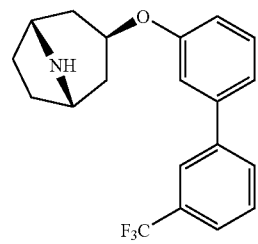

M.S. (ESI) (m/z): 348 [M+H]$^+$.

EXAMPLE IV.23

3-exo-(4'-Trifluoromethoxybiphenyl-3-yloxy)-8-azabicyclo[3.2.1]octane

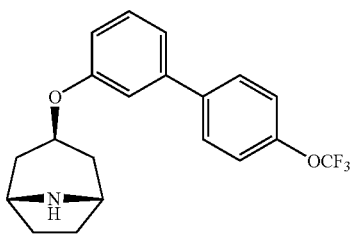

M.S. (ESI) (m/z): 364 [M+H]$^+$.

EXAMPLE IV.24

3-exo-(2'-Methoxybiphenyl-3-yloxy)-8-azabicyclo[3.2.1]octane

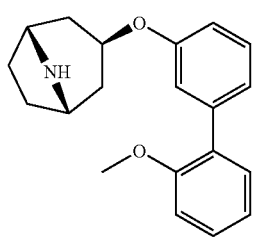

M.S. (ESI) (m/z): 310 [M+H]$^+$.

EXAMPLE IV.25

3-exo-(3'-Methoxybiphenyl-3-yloxy)-8-azabicyclo[3.2.1]octane

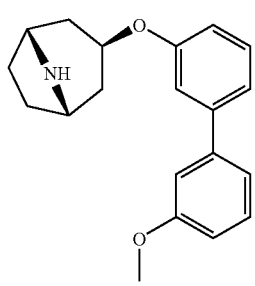

M.S. (ESI) (m/z): 310 [M+H]$^+$.

EXAMPLE IV.26

3-exo-(4'-Methoxybiphenyl-3-yloxy)-8-azabicyclo[3.2.1]octane

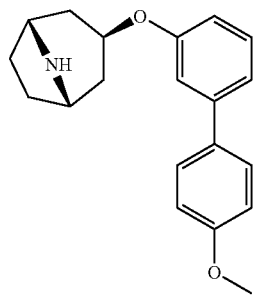

M.S. (ESI) (m/z): 310 [M+H]$^+$.

EXAMPLE IV.27

3-exo-(5-Phenylpyridin-3-yloxy)-8-azabicyclo[3.2.1]octane

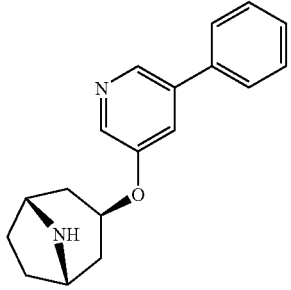

M.S. (ESI) (m/z): 281 [M+H]$^+$.

EXAMPLE IV.28

3-exo-(2-Fluorobiphenyl-3-yloxy)-8-azabicyclo[3.2.1]octane

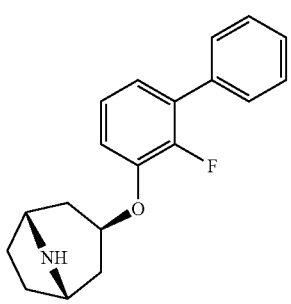

M.S. (ESI) (m/z): 298 [M+H]$^+$

EXAMPLE IV.29

3-exo-(4-Methylbiphenyl-3-yloxy)-8-azabicyclo[3.2.1]octane

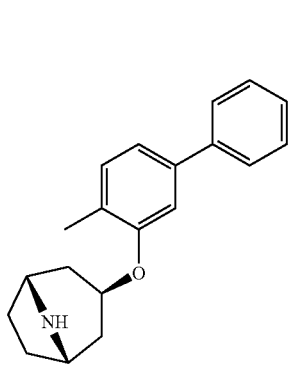

M.S. (ESI) (m/z): 294 [M+H]+.

EXAMPLE IV.30 exo 3'-(8-Azabicyclo[3.2.1]oct-3-yloxy)-2'-fluorobiphenyl-4-carbonitrile

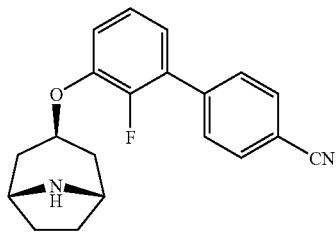

M.S. (ESI) (m/z): 323 [M+H]+.

EXAMPLE IV.31 exo 3-(2'-Trifluoromethoxybiphenyl-3-yloxy)-8-azabicyclo[3.2.1]octane

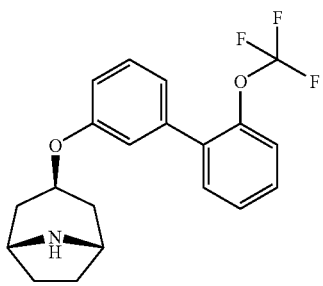

M.S. (ESI) (m/z): 364 [M+H]+.

EXAMPLE IV.32 exo 3'-(8-Azabicyclo[3.2.1]oct-3-yloxy)-biphenyl-3-carbonitrile

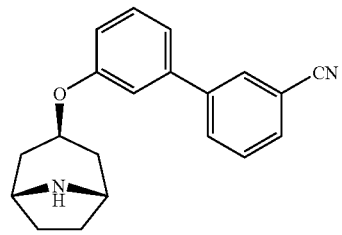

M.S. (ESI) (m/z): 305 [M+H]+.

Procedure V

EXAMPLE V.1 exo 3'-(8-Methyl-8-azabicyclo[3.2.1]oct-3-yloxy)biphenyl-4-carbonitrile

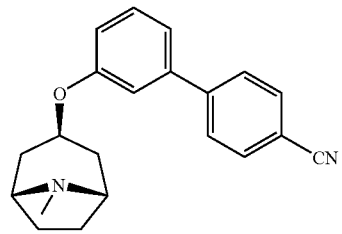

3'-(8-Azabicyclo[3.2.1]oct-3-exo-yloxy)biphenyl-4-carbonitrile (10 mg, 0.029 mmol) was dissolved in methanol (0.5 mL) and a solution of 37% formaldehyde in water (11.5 µL) was added. Sodium triacetoxyborohydride (12.5 mg) was added and the reaction stirred at ambient temperature for 2 h. DCM (3 mL) and 1N NaOH (aq) (3 mL) were then added to the reaction, the organic and aqueous layers were separated, and the organic layer was concentrated in vacuo. The crude product was purified by preparative LCMS to afford 3'-(8-methyl-8-azabicyclo[3.2.1]oct-3-exo-yloxy)biphenyl-4-carbonitrile as the trifluoroacetic acid salt (6.4 mg, 0.015 mmol, 52%) M.S. (ESI) (m/z): 319 [M+H]+.

Similarly prepared were:

EXAMPLE V.2

3-exo-(3-Chloro-5-phenoxyphenoxy)-8-methyl-8-azabicyclo[3.2.1]octane

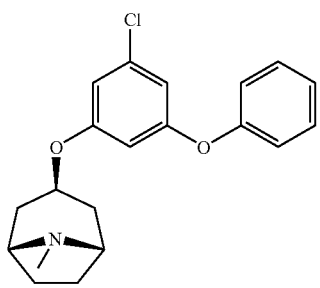

M.S. (ESI) (m/z): 344,346 [M+H]+.

Procedure VI

EXAMPLE VI.1

3-exo-(6-Methylbiphenyl-3-yloxy)-8-azabicyclo[3.2.1]octane

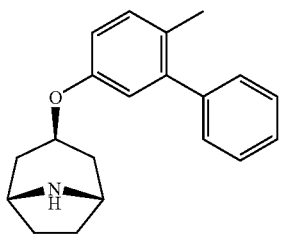

Potassium carbonate (659 mg, 4.27 mmol), phenylboronic acid (388 mg, 3.18 mmol), 2-bromo-4-fluorotoluene (0.20 mL, 1.59 mmol), and tetrakis(triphenylphosphine)palladium (0) (92 mg, 5mol %), in DME (3 mL) were sealed in a microwave vessel and heated at 80° C. for 1200s, then 120° C. for 1200s. Ethyl acetate (5 mL) was added and the reaction was filtered and concentrated in vacuo. The crude material was then purified by flash column chromatography on silica gel. Elution with 10:90 ethyl acetate:heptane afforded 3-fluoro-6-methylbiphenyl (253 mg, 1.36 mmol, 86%).

A solution of 3-exo-hydroxy-8-azabicyclo[3.2.1]octane-8-carboxylic acid tert-butyl ester (122 mg, 0.563 mmol) in DMF (1.5 mL) was added to a stirred suspension of 60% sodium hydride in mineral oil (22 mg, 0.536 mmol) in DMF (0.5 mL) under an atmosphere of nitrogen. The reaction was stirred at ambient temperature for 1 h. A solution of 3-fluoro-6-methylbiphenyl (50 mg, 0.268 mmol) in DMF (0.5 mL) was then added and the reaction was heated in a microwave at 180° C. for 1200 s. The reaction mixture was concentrated in vacuo, DCM (1 mL) and TFA (1 mL) were added, and the reaction was stirred for 2 h. The crude reaction mixture was loaded onto a SCX cartridge. The cartridge was eluted with methanol (3×10 mL) to remove impurities. Elution with ammonia in methanol (2M, 10 mL) followed by evaporation in vacuo afforded crude 3-exo-(6-methylbiphenyl-3-yloxy)-8-azabicyclo[3.2.1]octane. The crude material was then purified by preparative LCMS to afford 3-exo(6-methylbiphenyl-3-yloxy)-8-azabicyclo[3.2.1]octane as the trifluoroacetic acid salt (13 mg, 0.032 mmol, 12%). M.S. (ESI) (m/z): 294 [M+H]$^+$.

Similarly prepared were:

EXAMPLE VI.2

3-exo-(4-Methylbiphenyl-3-yloxy)-8-azabicyclo[3.2.1]octane

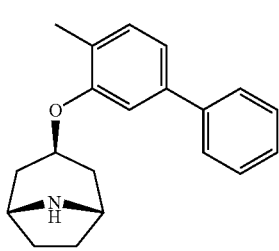

M.S. (ESI) (m/z): 294 [M+H]$^+$.

EXAMPLE VI.3

3-exo-(6-Trifluoromethylbiphenyl-3-yloxy)-8-azabicyclo[3.2.1]octane

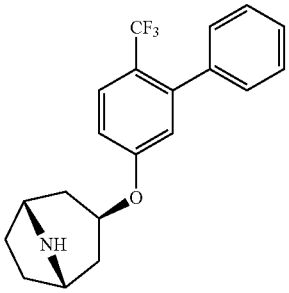

M.S. (ESI) (m/z): 348 [M+H]$^+$.

EXAMPLE VI.4 exo 3-(3-Fluoro-5-pyridin-4-ylphenoxy)-8-azabicyclo[3.2.1]octane

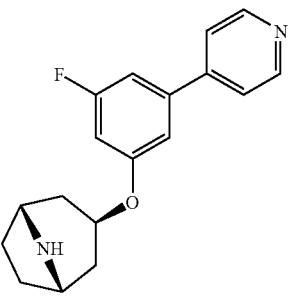

M.S. (ESI) (m/z): 299 [M+H]$^+$.

EXAMPLE VI.5 exo 3-(3-Chloro-5-pyridin-4-ylphenoxy)-8-azabicyclo[3.2.1]octane

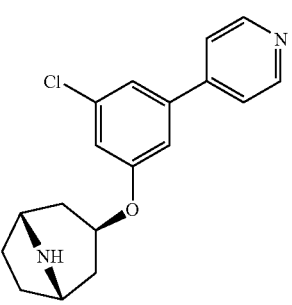

M.S. (ESI) (m/z): 315, 317 [M+H]$^+$.

EXAMPLE VI.6 exo 3-[4-Chloro-3-(pyridin-3-yloxy)phenoxy-8-azabicyclo[3.2.1]octane

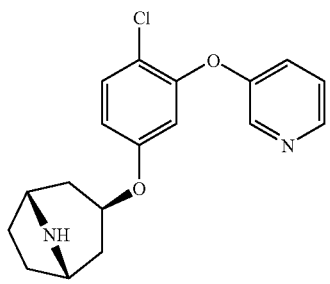

M.S. (ESI) (m/z): 315, 317 [M+H]+

EXAMPLE VI.7 exo 3-(4-Methyl-3-pyridin-4-ylphenoxy)-8-azabicyclo[3.2.1]octane

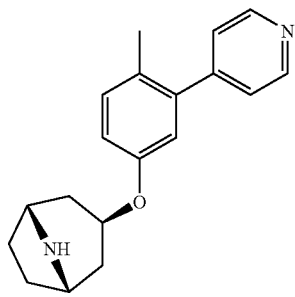

M.S. (ESI) (m/z): 295 [M+H]+.

EXAMPLE VI.8 exo 5-(8-Azabicyclo[3.2.1]oct-3-yloxy)-biphenyl-3,4'-dicarbonitrile

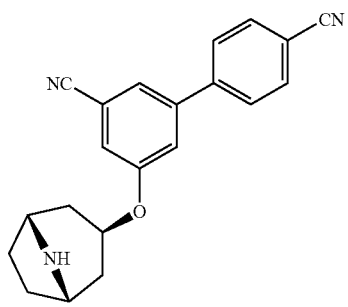

M.S. (ESI) (m/z): 330 [M+H]+.

EXAMPLE VI.9 exo 3'-(8-Azabicyclo[3.2.1]oct-3-yloxy)-5'-chlorobiphenyl-4-carbonitrile

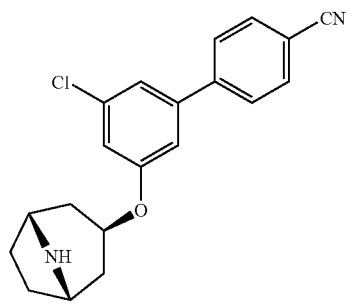

M.S. (ESI) (m/z): 339,341 [M+H]+. Procedure VII

EXAMPLE VIII.1

3-exo-(4-Chloro-6-Phenylpyridin-2-yloxy)-8-azabicyclo[3.2.1]octane

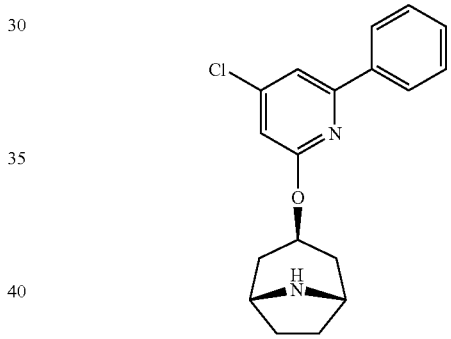

2,4-Dichloro-6-hydroxypyridine (696 mg, 4.2 mmol), 3-exo-hydroxy-8-azabicyclo[3.2.1]octane-8-carboxylic acid tert-butyl ester (965 mg, 4.2 mmol) and (4,4-Dimethyl-1,1-dioxido-1,2,5-thiadiazolidin-2-yl)triphenylphosphonium (4.31 g, 10.5 mmol) in THF (20 mL) were stirred for 16 h. Ethyl acetate (50 mL) and water (20 mL) were added and the organic and aqueous layers were separated. The organic layer was dried over Na$_2$SO$_4$ and concentrated in vacuo. The crude material was then purified by chromatography on silica gel. Elution with 10:90 ethyl acetate:heptane afforded 3-exo-(4,6-dichloropyridin-2-yloxy)-8-azabicyclo[3.2.1]octane-8-carboxylic acid tert-butyl ester (1.29 g, 3.6 mmol, 82%).

M.S. (ESI) m/z: 373,375 [M+H]+.

3-exo-(4,6-Dichloropyridin-2-yloxy)-8-azabicyclo[3.2.1]octane-8-carboxylic acid tert-butyl ester (200 mg, 0.54 mmol), phenylboronic acid (78 mg, 0.64 mmol), tetrakis(triphenylphosphine)palladium(0) (31 mg, 5mol %) and potassium carbonate (201 mg, 1.45 mmol) in DME (2.5 mL) were heated in the microwave at 100° C. for 900s. Ethyl acetate (20 mL) and water (10 mL) were added and the aqueous and organic layers were separated, dried over Na$_2$SO$_4$ and concentrated in vacuo. The crude material was then purified by chromatography on silica gel. Elution with 5:95 ethyl acetate:heptane afforded 3-exo-(4-chloro-6-phenylpyridin-2-yloxy)-8-azabicyclo[3.2.1]octane-8-carboxylic acid tert-butyl ester (68 mg, 0.16 mmol, 30%). M.S. (ESI) m/z: 415,417 [M+H]⁺.

3-exo-(4-chloro-6-phenylpyridin-2-yloxy)-8-azabicyclo[3.2.1]octane-8-carboxylic acid tert-butyl ester (30 mg, 0.072 mmol) was dissolved in DCM (2 mL) and TFA (2 mL) and stirred for 30 min and then the solvents were removed in vacuo. The crude material was then purified by preparative LCMS to afford 3-exo-(4-chloro-6-phenylpyridin-2-yloxy)-8-azabicyclo[3.2.1]octane as the trifluoroacetic acid salt (13 mg, 0.030 mmol, 42%). M.S. (ESI) m/z: 315,317 [M+H]⁺.

Similarly prepared were:

EXAMPLE VII.2

3-exo-(4,6-Diphenylpyridin-2-yloxy)-8-azabicyclo[3.2.1]octane

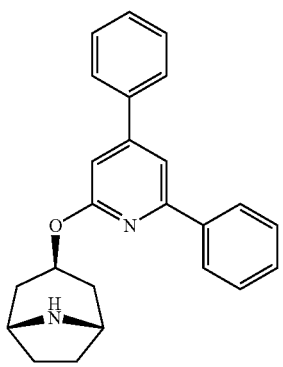

M.S. (ESI) m/z: 357 [M+H]⁺.

EXAMPLE VII.3 exo 4-[6-(8-Azabicyclo[3.2.1]oct-3-yloxy)-4-chloropyridin-2-yl]benzonitrile

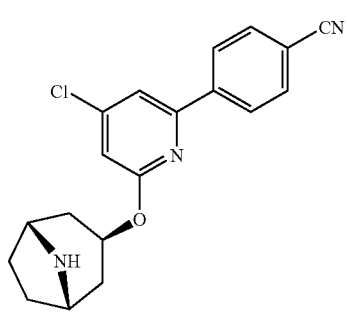

M.S. (ESI) m/z: 340,342 [M+H]⁺.

EXAMPLE VII.4 exo 4-[2-(8-Azabicyclo[3.2.1]oct-3-yloxy)-6-chloropyridin-4-yl]benzonitrile

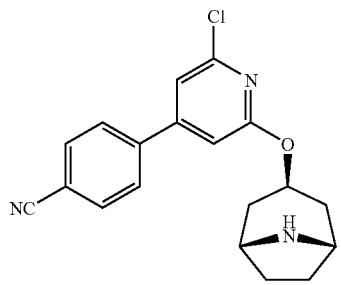

M.S. (ESI) m/z: 340,342 [M+H]⁺.

EXAMPLE VII.5

3-exo-(3-Pyridin-4-ylphenoxy)-8-azabicyclo[3.2.1]octane

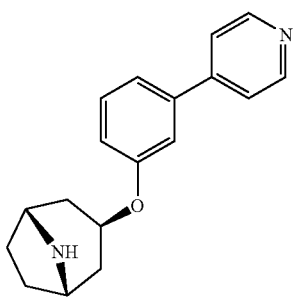

M.S. (ESI) m/z: 281 [M+H]⁺.

EXAMPLE VII.6 exo 4-[6-(8-Azabicyclo[3.2.1oct-3-yloxy)pyridin-2-yl]benzonitrile

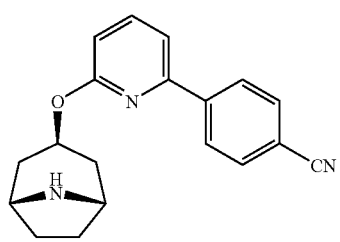

M.S. (ESI) m/z: 306 [M+H]⁺.

EXAMPLE VII.7 exo 2-{4-(8-Azabicyclo[3.2.1]oct-3-yloxy)-6-chloro-pyridin-2-yl}benzonitrile

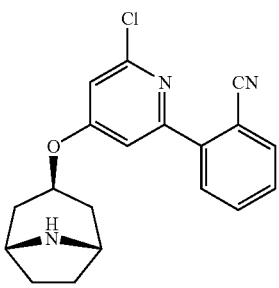

M.S. (ESI) m/z: 340,342 [M+H]$^+$.

EXAMPLE VII.8 exo 2-{6-(8-Azabicyclo[3.2.1]oct-3-yloxy)-4-chloro-pyridin-2-yl}benzonitrile

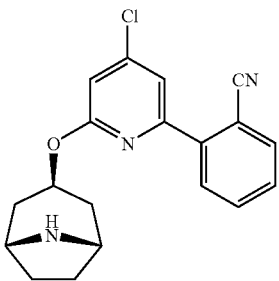

M.S. (ESI) m/z: 340,342 [M+H]$^+$.

EXAMPLE VII.9 exo 2-{6-(8-Azabicyclo[3.2.1]oct-3-yloxy)-4-chloro-pyridin-2-yl}benzamide

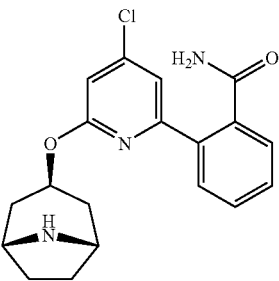

M.S. (ESI) m/z: 358,360 [M+H]$^+$.

EXAMPLE VII.10 exo 2-[2-(8-Azabicyclo[3.2.1]oct-3-yloxy)-6-chloro-pyridin-4-yl]benzonitrile

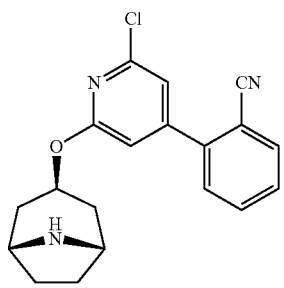

M.S. (ESI) m/z: 340,342 [M+H]$^+$.

EXAMPLE VII.11 exo 2-[6-(8-Azabicyclo[3.2.1]oct-3-yloxy)pyridin-2-yl]benzonitrile

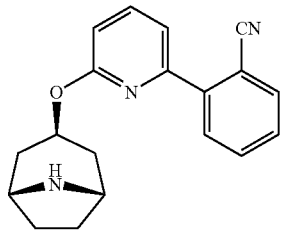

M.S. (ESI) m/z: 306 [M+H]$^+$.

EXAMPLE VII.12 exo 4-[2-(8-Azabicyclo[3.2.1]oct-3-yloxy)pyridin-4-yl]benzonitrile

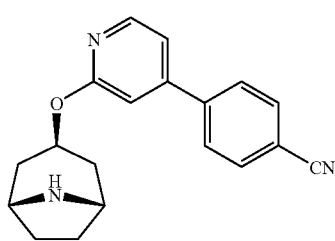

M.S. (ESI) m/z: 306 [M+H]$^+$.

EXAMPLE VII.13 exo 4-[4-(8-Azabicyclo[3.2.1]oct-3-yloxy)pyridin-2-yl]benzonitrile

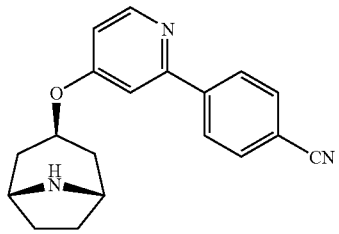

M.S. (ESI) m/z: 306 [M+H]$^+$.

EXAMPLE VII.14 exo 3-(4.5-Difluorobiphenyl-3-yloxy)-8-azabicyclo[3.2.1]octane

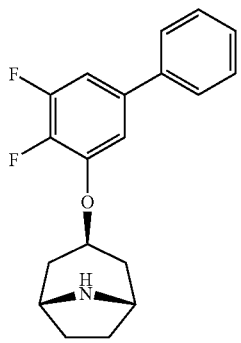

M.S. (ESI) m/z: 316 [M+H]$^+$.

EXAMPLE VII.15 exo 3-(5-Trifluoromethylbiphenyl-3-yloxy)-8-azabicyclo[3.2.1]octane

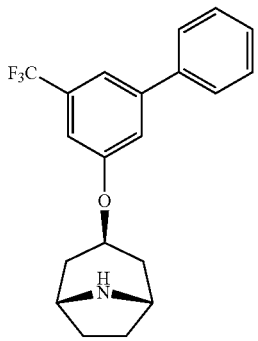

M.S. (ESI) m/z: 348 [M+H]$^+$.

Procedure VIII

EXAMPLE VIII.1

2-(8-Azabicyclo[3.2.1]oct-3-exo-yloxy)-6-phenyl-isonicotinonitrile

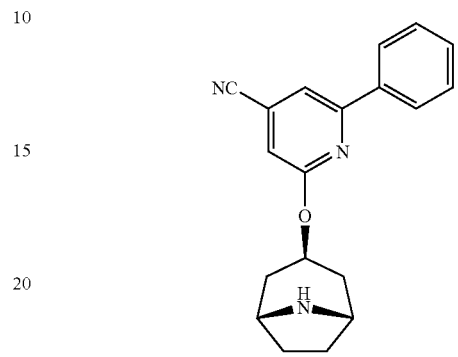

3-exo-(4-Chloro-6-pyridin-2-yloxy)-8-azabicyclo[3.2.1]octane-8-carboxylic acid tert-butyl ester (30 mg, 0.072 mmol) prepared as above, zinc(II) cyanide (5 mg, 0.043 mmol), and tetrakis(triphenylphosphine)palladium(0) (4.2 mg, 5mol %) in DMF (0.5 mL) were sealed in a microwave vessel and heated at 180° C. for 900s. The crude reaction mixture was filtered through a short pad of dicalite. The crude material was then purified by preparative LCMS to afford 3-exo(4-cyano-6-phenylpyridin-2-yloxy)-8-azabicyclo[3.2.1]octane-8-carboxylic acid tert-butyl ester (20 mg) which was treated directly with DCM (1 mL) and TFA (1 mL), stirred for 30 min and then the solvents were removed in vacuo. The crude material was purified by preparative LCMS to afford 2-(8-azabicyclo[3.2.1]oct-3-exo-yloxy)-6-phenyl-isonicotinonitrile as the trifluoroacetic acid salt (4.2 mg, 0.010 mmol, 14%). M.S. (ESI) m/z: 306 [M+H]$^+$.

Similarly prepared were:

EXAMPLE VIII.2 exo 2-(8-Azabicyclo[3.2.1]oct-3-yloxy)-6-(4-cyanophenyl)isonicotinonitrile

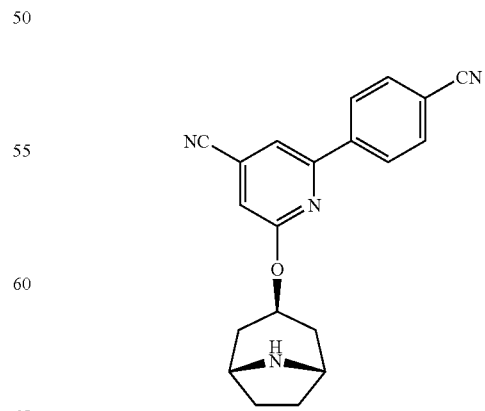

M.S. (ESI) m/z: 331 [M+H]$^+$.

EXAMPLE VIII.3 exo 2-(8-Azabicyclo[3.2.1]oct-3-yloxy)-6-(2-cyanophenyl)isonicotinonitrile

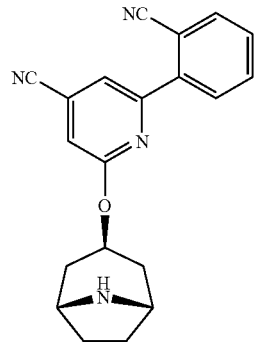

M.S. (ESI) m/z: 331 [M+H]⁺.

EXAMPLE VIII.4 exo 2-(8-Azabicyclo[3.2.1]oct-3-yloxy)-6-(2-trifluoromethylphenyl)isonicotinonitrile

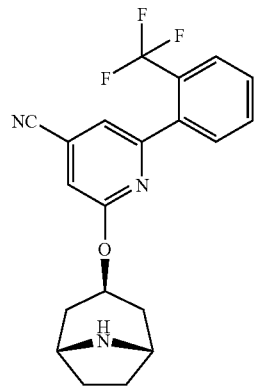

M.S. (ESI) m/z: 374 [M+H]⁺.

EXAMPLE VIII.5 exo 2-(8-Azabicyclo[3.2.1]oct-3-yloxy)-6-(2-methoxyphenyl)isonicotinonitrile

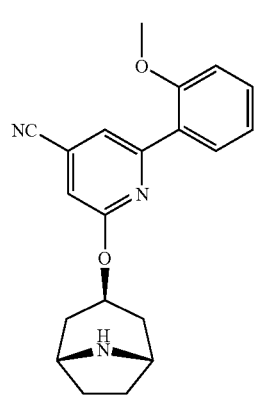

M.S. (ESI) m/z: 336 [M+H]⁺.

EXAMPLE VIII.6 exo 2-(6-(8-Azabicyclo[3.2.1]oct-3-yloxy)-4-chloropyridin-2-yl}benzoic acid

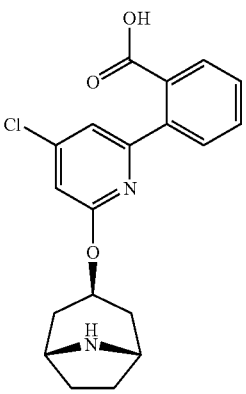

M.S. (ESI) m/z: 350 [M+H]⁺.

EXAMPLE VIII.7 exo 2-(8-Azabicyclo[3.2.1]oct-3-yloxy)-6-(3-fluorophenyl)isonicotinonitrile

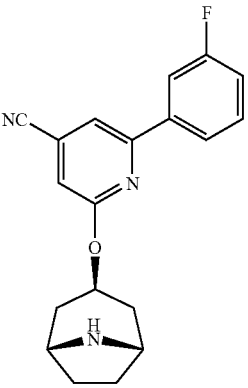

M.S. (ESI) m/z: 324 [M+H]⁺.

Procedure IX

EXAMPLE IX.1 exo 3-(8-Azabicyclo[3.2.1]oct-3-yloxy)-5-(3-fluoropyridin-2-yl)benzonitrile

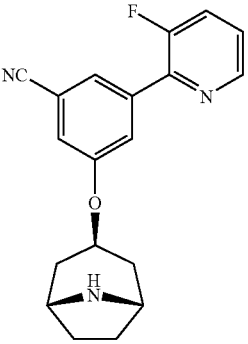

3-Bromo-5-fluorobenzonitrile (8.62 g, 43 mmol) was dissolved in DMF (20 mL). Sodium hydride (2.46 g, 62 mmol)

was added portionwise to the stirred solution under an atmosphere of nitrogen. Exo tert-Butyl 3-hydroxy-8-azabicyclo[3.2.1]octane-8-carboxylate (7.0 g, 31 mmol) was then added and then reaction was stirred at ambient temperature for 30 minutes. The reaction was quenched with water then the solution was extracted with DCM. The organic layers were combined and dried over $MgSO_4$. The organic layer was concentrated to leave a brown gum, which was dissolved in DCM (50 mL) and washed with water (3×40 mL). The organic layer was combined and dried over $MgSO_4$. The organic layer was concentrated in vacuo to leave a brown gum. The crude material was then purified by chromatography on silica gel. Elution with 10:90 ethyl acetate:heptane afforded exo tert-butyl 3-(3-bromo-5-cyanophenoxy)-8-azabicyclo[3.2.1]octane-8-carboxylate (7.23 g, 17.8 mmol, 58%) as a pale yellow solid.

Exo tert-butyl 3-(3-bromo-5-cyanophenoxy)-8-azabicyclo[3.2.1]octane-8-carboxylate (2.1 g, 5.2 mmol) in THF (20.6 ml) was treated with triisopropyl borate (3.3 ml, 2.7 g, 14 mmol,), followed by 1.6M n-butyllithium in hexane (4.0 mL, 6.4 mmol) over 5 minutes at −78° C., under an atmosphere of nitrogen. The reaction was stirred at −78° C. for 2 h then warmed to ambient temperature over 60 minutes. The reaction mixture was poured onto 2N HCl (20 mL). and extracted with diethyl ether. The combined organic extracts were concentrated in vacuo to afford the crude product. The crude product was purified over a short plug of silica gel using 25:75 ethyl acetate:heptane to remove impurities then methanol to afford exo 3-[8-(tert-butoxycarbonyl)-8-azabicyclo[3.2.1]oct-3-yloxy]-5-cyanophenylboronic acid (1.72 g, 4.6 mmol, 90%).

Exo 3-[8-(tert-butoxycarbonyl)-8-azabicyclo[3.2.1]oct-3-yloxy]-5-cyanophenylboronic acid (80 mg, 0.21 mmol), 2-chloro-3-fluoropyridine (22 mg, 17 µL, 0.2 mmol), $PCy_3$ (7.2 mg, 0.03 mmol), $Pd_2(dba)_3$ (6.5 mg, 7.1 µmol), and $K_3PO_4$ (78 mg, 0.37 mmol) were placed in a 5 mL microwave vessel followed by the addition of dioxane (2 mL) and water (0.5 mL). The vessel was then sealed. The reaction was heated at 100° C. for 600 seconds. The reaction was quenched by the addition of EtOAc (10 mL) and water (5 mL) and the aqueous and organic layers were separated. The organic layer was washed with water (2×5 mL), then dried over $MgSO_4$ and concentrated in vacuo. The crude material was then purified by chromatography on silica gel. Elution with 1:3 ethyl acetate:heptane afforded exo tert-butyl 3-[3-cyano-5-(3-fluoropyridin-2-yl)phenoxy]-8-azabicyclo[3.2.1]octe-8-carboxylate (84 mg, 0.20 mmol, 92%).

Exo tert-butyl 3-[3-cyano-5-(3-fluoropyridin-2-yl)phenoxy]-8-azabicyclo[3.2.1]octe-8-carboxylate (84 mg, 0.20 mmol) was dissolved in DCM (2 mL). TFA (1 mL) was added and the reaction was placed on a mechanical shaker for 1 hour. The solvents were then removed in vacuo. The crude reaction mixture was loaded onto a SCX cartridge. The cartridge was eluted with methanol (3×10 mL) to remove impurities. Elution with ammonia in methanol (2M, 10 mL) followed by evaporation in vacuo afforded exo 3-(8-azabicyclo[3.2.1]oct-3-yloxy)-5-(3-fluoropyridin-2-yl)benzonitrile (37 mg, 0.12 mmol, 58%).

M.S. (ESI) m/z: 324 [M+H]$^+$.

Similarly prepared were:

EXAMPLE IX.2 exo 3-(8-Azabicyclo[3.2.1]oct-3yloxy)-5-(3-chloropyridin-2-yl)benzonitrile

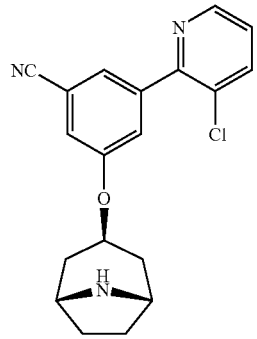

M.S. (ESI) m/z: 340, 342 [M+H]$^+$.

EXAMPLE IX.3 exo 6-(3-(8-Azabicyclo[3.2.1]oct-3-yloxy)-5-cyanophenyl)nicotinonitrile

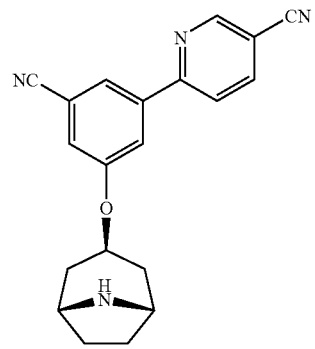

M.S. (ESI) m/z: 331 [M+H]$^+$.

EXAMPLE IX.4 exo 3-(8-Azabicyclo[3.2.1]oct-3-yloxy)-5-(3-(trifluoromethyl)pyridin-2-yl)benzonitrile

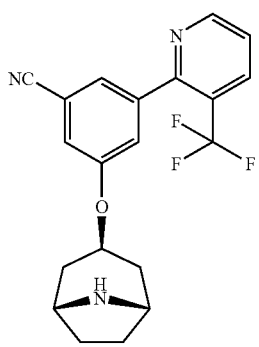

M.S. (ESI) m/z: 374 [M+H]$^+$.

EXAMPLE IX.5 exo 3-(8-Azabicyclo[3.2.1]oct-3-yloxy)-5-(pyridin-2-yl)benzonitrile

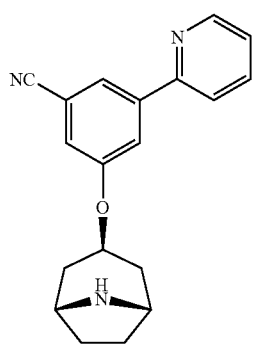

M.S. (ESI) m/z: 306 [M+H]$^+$.

EXAMPLE IX.6 exo 3-(8-Azabicyclo[3.2.1]oct-3-yloxy)-5-(3,5-dichloropyridin-2-yl)benzonitrile

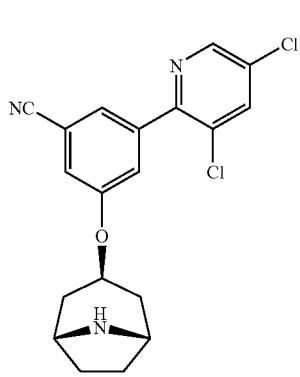

M.S. (ESI) m/z: 374,376,378 [M+H]$^+$.

EXAMPLE IX.7 exo 3-(8-Azabicyclo[3.2.1]oct-3-yloxy)-5-(3-methoxypyridin-2-yl)benzonitrile

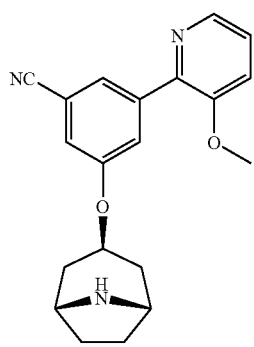

M.S. (ESI) m/z: 336 [M+H]$^+$.

EXAMPLE IX.8 exo N-(2-(8-Azabicyclo[3.2.1]oct-3-yloxy)-5-cyanophenyl)pyridin-3-yl)acetamide

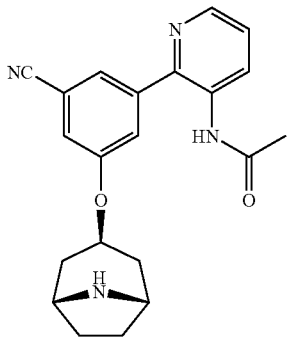

M.S. (ESI) m/z: 363 [M+H]$^+$.

EXAMPLE IX.9 exo 3-(8-Azabicyclo[3.2.1]oct-3-yloxy)-5-cyanophenyl)nicotinonitrile

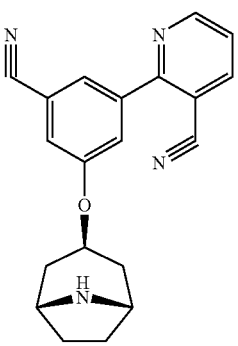

M.S. (ESI) m/z: 331 [M+H]$^+$.

EXAMPLE IX.10 exo 3-(8-Azabicyclo[3.2.1]oct-3-yloxy)-5-(pyrimidin-2-yl)benzonitrile

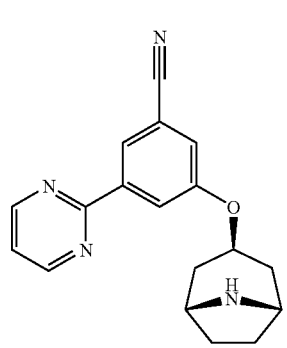

M.S. (ESI) m/z: 307 [M+H]$^+$.

EXAMPLE IX.11 exo 3-(8-Azabicyclo3.2.1]oct-3-yloxy)-5-(Pyrimidin-5-yl)benzonitrile

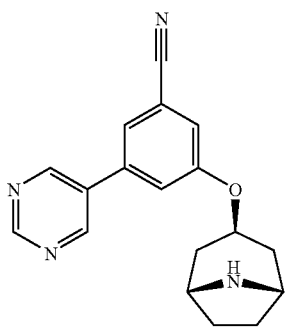

M.S. (ESI) m/z: 307 [M+H]+.

EXAMPLE IX.12 exo 3-(8-Azabicyclo[3.2.1]oct-3-yloxy)-5-(isoquinolin-1-yl)benzonitrile

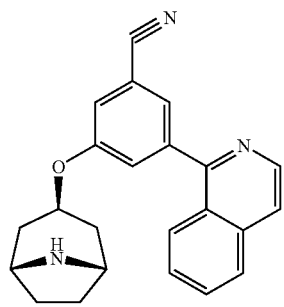

M.S. (ESI) m/z: 356 [M+H]+.

Procedure X

EXAMPLE X.1

3-exo-(5-Chloro-6-phenoxypyridin-2-yloxy)-8-azabicyclo[3.2.1]octane

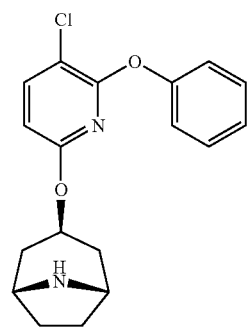

Exo tert-butyl 3-(5,6-dichloropyridin-2-yloxy)-8-azabicyclo[3.2.1]octane-8-carboxylate (150 mg, 0.4 mmol) prepared according to general procedure I was dissolved in DMA (0.5 mL) and added to a solution of phenol (56 mg, 0.6 mmol) and sodium hydride (60% in mineral oil, 15 mg, 0.6 mmol) in DMA (0.5 mL). The reaction was heated to 180° C. for 900s using microwave irradiation. Sodium hydride (60% in mineral oil, 10 mg, 0.4 mmol) was added and the reaction was heated to 180° C. for a further 900s using microwave irradiation. The reaction was quenched by the addition of 1M aqueous NaOH (5 mL) and extracted into DCM (10 mL). The organic layer was dried over $Na_2SO_4$ and concentrated in vacuo. The crude material was then purified by chromatography on silica gel. Elution with 20:80 ethyl acetate:heptane afforded exo tert-butyl 3-(5-chloro-6-phenoxypyridin-2-yloxy)-8-azabicyclo[3.2.1]octane-8-carboxylate (77 mg, 0.1 8 mmol, 45%)

Exo tert-butyl 3-(5-chloro-6-phenoxypyridin-2-yloxy)-8-azabicyclo[3.2.1]octane-8-carboxylate (77 mg, 0.18 mmol) was dissolved in DCM (2 mL) and TFA (1 mL) and stirred at ambient temperature for 1 h. Solvents were removed in vacuo and the crude material was purified by preparative LCMS to afford 3-exo-(5-chloro-6-phenoxypyridin-2-yloxy)-8-azabicyclo[3.2.1]octane (7.1 mg, 0.02 mmol, 9%). M.S. (ESI) m/z: 331,333 [M+H]+.

Similarly prepared were:

EXAMPLE X.2

3-exo-(6-Phenoxypyridin-2-yloxy)-8-azabicyclo[3.2.1]octane

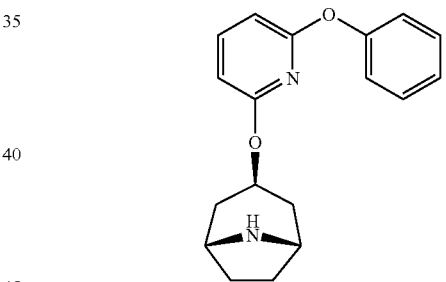

M.S. (ESI) m/z: 297 [M+H]+.

Procedure XI:

Assay of Monoamine Uptake

The in vitro test for the inhibition of dopamine and serotonin uptake was performed in Chinese Hamster Ovary cells expressing the human dopamine transporter (hDAT) or the human serotonin transporter (hSERT). The in vitro test for the inhibition of noradrenaline uptake was performed in Madin Darby Canine Kidney Cells (MDCK) expressing the human noradrenaline transporter (hNET). Briefly, cell lines stably overexpressing the appropriate human transporter were propagated and plated according to standard cell culture techniques. Following plating, cells were left to adhere for either one or two days. A 6-point serial dilution (normally 1E-5M to 1E-10M) of test and reference compounds was prepared, added to the washed cells and incubated for 5 minutes at ambient temperature for dopamine or serotonin transporter overexpressing and 37° C. for noradrenaline overexpressing cells. Next, a final concentration of 20 nM of appropriate neurotransmitter (mixture of [3H]-neurotransmitter and nonlabelled neurtoransmitter) was added and the cells were incubated for three or five minutes at ambient temperature for dopamine or serotonin transporter overexpressing cells or ten minutes at 37° C. for noradrenaline overexpressing cells. Following termination of the assay, Microscint-20 was added directly to the cells and the amount of radioactivity taken up by the cells was estimated by scintillation counting.

$pEC_{50}$ values indicating inhibition of monoamine uptake were calculated using standard curve fitting techniques.

Table 1 indicates the potency of the representative compounds of the invention.

TABLE 1

| Example | Chemical name | hDAT | hNET | hSERT |
|---|---|---|---|---|
| IV.19 | exo 3-(3-Chloro-5-phenoxyphenoxy)-8-azabicyclo[3.2.1]octane | (+++) | (+++) | (+) |
| IV.8 | exo 3-(2'-Trifluoromethylbiphenyl-3-yloxy)-8-azabicyclo[3.2.1]octane | (+) | (+++) | (++) |
| IX.3 | exo 6-(3-(8-Azabicyclo[3.2.1]oct-3-yloxy)-5-cyanophenyl)nicotinonitrile | (+) | (+) | (+++) |
| I.7 | 3-(5-Fluorobiphenyl-3-yloxy)-8-azabicyclo[3.2.1]octane | (+) | (+++) | (++) |
| III.5 | 3-endo-(3-Phenoxyphenoxy)-8-azabicyclo[3.2.1]octane | (+++) | (++) | (+) |
| IV.9 | 3-exo-(2-Fluoro-3-methoxy-5-phenoxyphenoxy)-8-azabicyclo[3.2.1]octane | (+++) | (+++) | (+) |
| VI.8 | exo 5-(8-Azabicyclo[3.2.1]oct-3-yloxy)-biphenyl-3,4'-dicarbonitrile | (+) | (+) | (+++) |
| VI.3 | 3-exo-(6-Trifluoromethylbiphenyl-3-yloxy)-8-azabicyclo[3.2.1]octane | (+) | (+) | (++) |

+++ $pEC_{50} > 7$
++ $pEC_{50}$ 6-7
+ $pEC_{50} < 6$

We claim:

1. An 8-azabicyclo[3.2.1]octane derivative of Formula I,

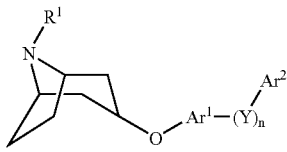

Formula I wherein
R$^1$ is H or C$_{1-5}$alkyl;
Y is O or S;
m is 1 or 2;
n is 0 or 1;
Ar$^1$ is phenylene or pyridylene, said phenylene and pyridylene being 1,3-linked with respect to O and when n is 1 with Y and when n is 0 with Ar$^2$, said phenylene or pyridylene being optionally substituted with one or two substituents independently selected from halogen, C$_{1-5}$alkyl, C$_{1-5}$alkoxy, C$_{3-6}$cycloalkyl, C$_{2-5}$alkenyl, C$_{2-5}$alkynyl, phenyl, CN and hydroxy, wherein said C$_{1-5}$alkyl and C$_{1-5}$alkoxy are optionally substituted with one to three halogens and wherein the oxygen of said hydroxy is optionally bonded to Ar$^2$ to form a 5-membered ring;
Ar$^2$ is phenyl or a 5-6 membered heteroaryl, said phenyl or 5-6 membered heteroaryl being optionally substituted with one to three substituents independently selected from halogen, C$_{1-5}$alkyl, C$_{1-5}$alkoxy, CN, CONR$^2$R$^3$, CO$_2$R$^4$, NHCOR$^5$ and hydroxy, wherein said C$_{1-5}$alkyl and C$_{1-5}$alkoxy are optionally substituted with one to three halogens and wherein the oxygen of said hydroxy is optionally bonded to Ar$^1$ to form a 5-membered ring;
R$^2$-R$^4$ are independently H or C$_{1-5}$alkyl and
R$^5$ is C$_{1-5}$alkyl;
or a pharmaceutically acceptable salt thereof.

2. The 8-azabicyclo[3.2.1]octane derivative according to claim 1, wherein R$^1$ is H or methyl.

3. The 8-azabicyclo[3.2.1]octane derivative according to claim 1, wherein n is 0.

4. The 8-azabicyclo[3.2.1]octane derivative according to claim 1, wherein Y is O and n is 1.

5. The 8-azabicyclo[3.2.1]octane derivative according to claim 1, wherein Ar$^1$ is phenyl or pyridyl optionally substituted with 1-2 substituents selected from chloro, fluoro, methyl, methoxy or CN.

6. The 8-azabicyclo[3.2.1]octane derivative according to claim 1, wherein Ar$^2$ is phenyl or pyridyl optionally substituted with 1-2 substituents selected from chloro, fluoro, methyl, methoxy, CN or CF$_3$.

7. A 8-azabicyclo[3.2.1]octane derivative selected from:
3-exo-(5-chlorobiphenyl-3-yloxy)-8-azabicyclo[3.2.1]octane;
exo 5-(8-azabicyclo[3.2.1]oct-3-yloxy)biphenyl-3-carbonitrile;
exo 3-(8-azabicyclo[3.2.1]oct-3-yloxy)-5-phenoxybenzonitrile;
3-exo-(4'-methoxybiphenyl-3-yloxy)-8-azabicyclo[3.2.1]octane;
exo 3'-(8-azabicyclo[3.2.1]oct-3-yloxy)biphenyl-4-carbonitrile;
3-exo-(3-pyridin-4-ylphenoxy)-8-azabicyclo[3.2.1]octane;
exo 2-{6-(8-azabicyclo[3.2.1]oct-3-yloxy)-4-chloropyridin-2-yl}benzonitrile;
exo 2-(8-azabicyclo[3.2.1]oct-3-yloxy)-6-(2-cyanophenyl)isonicotinonitrile;
exo 3-[(8-azabicyclo[3.2.1]oct-3-yl)oxy]-5-(3-chloropyridin-2-yl)benzonitrile;
exo 3-(8-azabicyclo[3.2.1]oct-3-yloxy)-5-cyanophenyl)nicotinonitrile;
exo 3-(8-azabicyclo[3.2.1]oct-3-yloxy)-5-(3-fluoropyridin-2-yl)benzonitrile;

exo 3'-(8-azabicyclo[3.2.1]oct-3-yloxy)biphenyl-2-carbonitrile;

exo 2-[6-(8-azabicyclo[3.2.1]oct-3-yloxy)pyridin-2-yl]benzonitrile;

3'-(8-azabicyclo[3.2.1]oct-3-exo-yloxy)-2'-fluorobiphenyl-4-carbonitrile and 2-(8-azabicyclo[3.2.1]oct-3-exo-yloxy)-6-phenylisonicotinonitrile or a pharmaceutically acceptable salt thereof.

8. A pharmaceutical composition comprising an 8-azabicyclo [3.2.1]octane derivative or a pharmaceutically acceptable salt thereof according to claim 1 in admixture with one or more pharmaceutically acceptable auxiliaries.

9. A method of treating a disease or disorder in a mammal which is responsive to monoamine neurotransmitter reuptake in the nervous system, wherein the disease or disorder is selected from the group consisting of depression or pain, the method comprising administering to the mammal an effective amount of the 8-azabicyclo[3.2.1]octane derivative or a pharmaceutically acceptable salt thereof according to claim 1.

10. The method according to claim 9, wherein the mammal is a human.

11. The pharmaceutical composition according to claim 8, wherein the the 8-azabicycio [3.2.1]octane derivative is selected from the group consisting of 3-exo-(5-chlorobiphenyl-3-yloxy)-8-azabicyclo[3.2.1]octane;

exo 5-(8-azabicyclo[3.2.1]oct-3-yloxy)biphenyl-3-carbonitrile;

exo 3-(8-azabicyclo[3.2.1]oct-3-yloxy)-5-phenoxybenzonitrile;

3-exo-(4'-methoxybiphenyl-3-yloxy)-8-azabicyclo[3.2.1]octane;

exo 3'-(8-azabicyclo[3.2.1]oct-3-yloxy)biphenyl-4-carbonitrile:

3-exo-(3-pyridin-4-ylphenoxy)-8-azabicyclo[3.2.1]octane;

exo 2-{6-(8-azabicyclo[3.2.1]oct-3-yloxy)-4-chloropyridin-2-yl}benzonitrile;

exo 2-(8-azabicyclo[3.2.1]oct-3-yloxy)-6-(2-cyanophenyl)isonicotinonitrile;

exo 3-[(8-azabicyclo[3.2.1]oct-3-yl)oxy]-5-(3-chloropyridin-2-yl)benzonitrile;

exo 3-(8-azabicyclo[3.2.1]oct-3-yloxy)-5-cyanophenyl)nicotinonitrile;

exo 3-(8-azabicyclo[3.2.1]oct-3-yloxy)-5-(3-fluoropyridin-2-yl)benzonitrile;

exo 3'-(8-azabicyclo[3.2.1]oct-3-yloxy)biphenyl-2-carbonitrile;

exo 2[6-(8azabicyclo[3.2.1]oct-3-yloxy)pyridin-2-yl]benzonitrile;

3'-(8-azabicyclo[3.2.1]oct-3-exo-yloxy)-2'-fluorobiphenyi-4-carbonitrile and 2-(8-azabicyclo [3.2.1]oct-3-exo-yloxy)-6-phenylisonicotinonitrile or a pharmaceutically acceptable salt thereof 12. The method according to claim 9, wherein the the 8-azabicyclol [3.2.]octane derivative is selected from the group consisting of 3-exo-(5-chlorobiphenyl-3-yloxy)-8-azabicyclo[3.2.1]octane;

exo 5-(8-azabicyclo[3.2.1]oct-3-yloxy)biphenyl-3-carbonitrile;

exo 3-(8-azabicyclo[3.2.1]oct-3-yloxy)-5-phenoxybenzonitrile;

3-exo-(4'-methoxybiphenyl-3-yloxy)-8-azabicyclo[3.2.1]octane;

exo 3'-(8-azabicyclo[3.2.1]oct-3-yloxy)biphenyl-4-carbonitrile;

3-exo-(3-pyridin-4-ylphenoxy)-8-azabicyclo[3.2.1]octane;

exo 2-{6-(8-azabicyclo[3.2.1]oct-3-yloxy)-4-chloropyridin-2-yl}benzonitrile;

exo 2-(8-azabicyclo[3.2.1]oct-3-yloxy)-6-(2-cyanophenyl)isonicotinonitrile;

exo 3-[(8-azabicyclo[3.2.1]oct-3-yl)oxy]-5-(3-chloropyridin-2-yl)benzonitrile;

exo 3-(8-azabicyclo[3.2.1]oct-3-yloxy)-5-cyanophenyl) nicotinonitrile;

exo 3-(8-azabicyclo[3.2.1]oct-3-yloxy)-5-(3-fluoropyridin-2-yl)benzonitrile;

exo 3'-(8-azabicyclo[3.2.1]oct-3-yloxy)biphenyl-2-carbonitrile;

exo 2[6-(8azabicyclo[3.2.1]oct-3-yloxy)pyridin-2-yl]benzonitrile;

3'-(8-azabicyclo[3.2.1]oct-3-exo-yloxy)-2'-fluorobiphenyi-4-carbonitrile and 2-(8-azabicyclo [3.2.1]oct-3-exo-yloxy)-6-phenylisonicotinonitrile or a pharmaceutically acceptable salt thereof 13. The method according to claim 9, wherein the disease or disorder is depression.

14. The method according to claim 9, wherein the disease or disorder is pain.

* * * * *